(12) United States Patent
Gu et al.

(10) Patent No.: US 12,053,523 B2
(45) Date of Patent: Aug. 6, 2024

(54) COMPOSITIONS COMPRISING CHEMOTHERAPEUTIC AGENTS AND CHECKPOINT INHIBITORS AND METHODS OF USE

(71) Applicant: NORTH CAROLINA STATE UNIVERSITY, Raleigh, NC (US)

(72) Inventors: Zhen Gu, Los Angeles, CA (US); Chao Wang, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 491 days.

(21) Appl. No.: 16/772,381

(22) PCT Filed: Dec. 13, 2018

(86) PCT No.: PCT/US2018/065382
§ 371 (c)(1),
(2) Date: Jun. 12, 2020

(87) PCT Pub. No.: WO2019/118686
PCT Pub. Date: Jun. 20, 2019

(65) Prior Publication Data
US 2021/0077620 A1 Mar. 18, 2021

Related U.S. Application Data

(60) Provisional application No. 62/598,254, filed on Dec. 13, 2017.

(51) Int. Cl.
*A61P 35/00* (2006.01)
*A61K 9/00* (2006.01)
*A61K 31/7068* (2006.01)
*A61K 38/17* (2006.01)
*A61K 39/395* (2006.01)

(52) U.S. Cl.
CPC ........ *A61K 39/3955* (2013.01); *A61K 9/0024* (2013.01); *A61K 31/7068* (2013.01); *A61K 38/1709* (2013.01); *A61P 35/00* (2018.01)

(58) Field of Classification Search
CPC .............. A61K 39/3955; A61K 9/0024; A61K 31/7068; A61K 38/1709; A61P 35/00
USPC ..................................................... 424/134.1
See application file for complete search history.

(56) References Cited

U.S. PATENT DOCUMENTS

| | | |
|---|---|---|
| 3,610,795 A | 10/1971 | Antoine |
| 4,342,566 A | 8/1982 | Theofilopoulos |
| 4,816,567 A | 3/1989 | Cabilly et al. |
| 5,565,332 A | 10/1996 | Hoogenboom et al. |
| 5,721,367 A | 2/1998 | Kay et al. |
| 5,804,440 A | 9/1998 | Burton et al. |
| 5,837,243 A | 11/1998 | Deo et al. |
| 5,939,598 A | 8/1999 | Kucherlapati et al. |
| 6,096,441 A | 8/2000 | Hauser et al. |
| 6,130,364 A | 10/2000 | Jakobovits et al. |
| 6,180,377 B1 | 1/2001 | Morgan et al. |
| 2014/0099254 A1 | 4/2014 | Chang et al. |
| 2017/0007696 A1* | 1/2017 | Zhao .................... C07K 14/001 |
| 2017/0115275 A1 | 4/2017 | Rege et al. |
| 2017/0136127 A1 | 5/2017 | Maki et al. |

FOREIGN PATENT DOCUMENTS

| | | |
|---|---|---|
| CN | 105983097 A | 10/2016 |
| CN | 106994117 A | 8/2017 |
| WO | 94/29348 | 12/1994 |
| WO | 2015/168379 A2 | 11/2015 |
| WO | 2016/023979 A | 2/2016 |
| WO | 2016/176620 A1 | 11/2016 |
| WO | 2017/175200 A1 | 10/2017 |
| WO | 2017177179 A | 10/2017 |
| WO | 2018/078620 A1 | 5/2018 |
| WO | 2019/217954 A1 | 11/2019 |

OTHER PUBLICATIONS

International Search Report and Written Opinion issued in corresponding application No. PCT/US2018/065382, dated May 3, 2019, 11 pages.
Gupta et al. 'Cell Protective, ABC Triblock Polymer—Based Thermoresponsive Hydrogels with ROS-triggered Degradation and Drug Release', Journal of American Chemical Society, 2014, vol. 136, pp. 14896-14902.
Liang et al. 'ROS-responsive Drug Delivery Systems', AIChE Bioengineering and Translational Medicine, 2016, vol. 1, pp. 239-251.
J. Vegas, O. Veiseh, J. C. Doloff, M. Ma, H. H. Tam, K. Bratlie, J. Li, A. R. Bader, E. Langan, K. Olejnik, Combinatorial hydrogel library enables identification of materials that mitigate the foreign body response in primates. Nat. Biotechnol. 34, 345-352 (2016).
M. Cook, W. J. Lesterhuis, A. K. Nowak, R. A. Lake, Chemotherapy and immunotherapy: mapping the road ahead. Curr. Opin. Immunol. 39, 23-29 (2016).
M. Rosales, K. S. Anseth, The design of reversible hydrogels to capture extracellular matrix dynamics. Nat. Rev. Mater. 1, 15012 (2016).
A. Pulaski, S. Ostrand-Rosenberg, Mouse 4T1 breast tumor model. Curr. Protoc. Immunol., 20.22. 21-20.22. 16 (2001).

(Continued)

*Primary Examiner* — Yan Xiao
(74) *Attorney, Agent, or Firm* — Meunier Carlin & Curfman LLC

(57) ABSTRACT

Disclosed herein are methods of treating/inhibiting/reducing a non-immunogenic cancer in a subject or inducing blockade inhibitor susceptibility (such as, for example, PD-1/PDLI, CTLA-4/B7-1/2, and/or CD47/SIRPa inhibitor susceptibility) in a tumor in a subject with a cancer, said methods comprising administering to the subject a hydrogel matrix comprising a chemotherapeutic agent (including, but not limited to gemcitabine) and a blockade inhibitor (including, but not limited to a PD-1/PD-LI blockade inhibitor, such as, for example nivolumab, pembrolizumab, pidilizumab, atezolizumab, avelumab, durvalumab, and BMS-936559; a CTLA-4/B7-1/2 inhibitor such as, for example, Ipilimumab; and/or a CD47/SIRPa inhibitor such as, for example Hu5F9-G4, CVI, B6H12, 2D3, CC-90002, and TTI-621).

4 Claims, 14 Drawing Sheets

(56) References Cited

OTHER PUBLICATIONS

Boutros, A. Tarhini, E. Routier, O. Lambotte, F. L. Ladurie, F. Carbonnel, H. Izzeddine, A. Marabelle, S. Champiat, A. Berdelou, E. Lanoy, M. Texier, C. Libenciuc, A. M. Eggermont, J. C. Soria, C. Mateus, C. Robert, Safety profiles of anti-CTLA-4 and anti-PD-1 antibodies alone and in combination. Nat. Rev. Clin. Oncol. 13, 473-486 (2016).
Dunnill, T. Patton, J. Brennan, J. Barrett, M. Dryden, J. Cooke, D. Leaper, N. T. Georgopoulos, Reactive oxygen species (ROS) and wound healing: the functional role of ROS and emerging ROS-modulating technologies for augmentation of the healing process. Int. Wound J. 14, 89-96 (2017).
Nathan, A. Cunningham-Bussel, Beyond oxidative stress: an immunologist's guide to reactive oxygen species. Nat. Rev. Immunol. 13, 349-361 (2013).
Pfirschke, C. Engblom, S. Rickelt, V. Cortez-Retamozo, C. Garris, F. Pucci, T. Yamazaki, V. Poirier-Colame, A. Newton, Y. Redouane, Y. J. Lin, G. Wojtkiewicz, Y. Iwamoto, M. Mino-Kenudson, T. G. Huynh, R. O. Hynes, G. J. Freeman, G. Kroemer, L. Zitvogel, R. Weissleder, M. J. Pittet, Immunogenic Chemotherapy Sensitizes Tumors to Checkpoint Blockade Therapy. Immunity 44, 343-354 (2016).
Wang, W. Sun, Y. Ye, Q. Hu, H. N. Bomba, Z. Gu, In situ activation of platelets with checkpoint inhibitors for post-surgical cancer immunotherapy. Nat. Biomed. Eng. 1, 0011 (2017).
Wang, Y. Ye, G. M. Hochu, H. Sadeghifar, Z. Gu, Enhanced Cancer Immunotherapy by Microneedle Patch-Assisted Delivery of Anti-PD1 Antibody. Nano Lett. 16, 2334-2340 (2016).
Wang, Y. Ye, Q. Hu, A. Bellotti, Z. Gu, Tailoring Biomaterials for Cancer Immunotherapy: Emerging Trends and Future Outlook. Adv. Mater., (2017).
B. Johnson, J. M. Balko, M. L. Compton, S. Chalkias, J. Gorham, Y. Xu, M. Hicks, I. Puzanov, M. R. Alexander, T. L. Bloomer, J. R. Becker, D. A. Slosky, E. J. Phillips, M. A. Pilkinton, L. Craig-Owens, N. Kola, G. Plautz, D. S. Reshef, J. S. Deutsch, R. P. Deering, B. A. Olenchock, A. H. Lichtman, D. M. Roden, C. E. Seidman, I. J. Koralnik, J. G. Seidman, R. D. Hoffman, J. M. Taube, L. A. Diaz, Jr., R. A. Anders, J. A. Sosman, J. J. Moslehi, Fulminant Myocarditis with Combination Immune Checkpoint Blockade. N. Engl. J. Med. 375, 1749-1755 (2016).
I. Gabrilovich, S. Nagaraj, Myeloid-derived suppressor cells as regulators of the immune system. Nat. Rev. Immunol. 9, 162-174 (2009).
Killock, Lung cancer: Anti-PD-1 therapy in the frontline. Nat. Rev. Clin. Oncol. 13, 715 (2016).
Mathios, J. E. Kim, A. Mangraviti, J. Phallen, C.-K. Park, C. M. Jackson, T. Garzon-Muvdi, E. Kim, D. Theodros, M. Polanczyk, Anti-PD-1 antitumor immunity is enhanced by local and abrogated by systemic chemotherapy in GBM. Sci. Transl. Med. 8, 370ra180-370ra180 (2016).
R. Littman, Releasing the Brakes on Cancer Immunotherapy. Cell 162, 1186-1190 (2015).
Eriksson, J. Wenthe, S. Irenaeus, A. Loskog, G. Ullenhag, Gemcitabine reduces MDSCs, tregs and TGFβ-1 while restoring the teff/treg ratio in patients with pancreatic cancer. J. Transl. Med. 14, 282 (2016).
I. Buchbinder, F. S. Hodi, Melanoma in 2015: Immune-checkpoint blockade—durable cancer control. Nat. Rev. Clin. Oncol. 13, 77-78 (2016).
Nolan, P. Savas, A. N. Policheni, P. K. Darcy, F. Vaillant, C. P. Mintoff, S. Dushyanthen, M. Mansour, J.-M. B. Pang, S. B. Fox, Combined immune checkpoint blockade as a therapeutic strategy for BRCA1-mutated breast cancer. Sci. Transl. Med. 9, eaal4922 (2017).
Vacchelli, Y. Ma, E. E. Baracco, A. Sistigu, D. P. Enot, F. Pietrocola, H. Yang, S. Adjemian, K. Chaba, M. Semeraro, M. Signore, A. De Ninno, V. Lucarini, F. Peschiaroli, L. Businaro, A. Gerardino, G. Manic, T. Ulas, P. Gunther, J. L. Schultze, O. Kepp, G. Stoll, C. Lefebvre, C. Mulot, F. Castoldi, S. Rusakiewicz, S. Ladoire, L. Apetoh, J. M. Bravo-San Pedro, M. Lucattelli, C. Delarasse, V. Boige, M. Ducreux, S. Delaloge, C. Borg, F. Andre, G. Schiavoni, I. Vitale, P. Laurent-Puig, F. Mattei, L. Zitvogel, G. Kroemer, Chemotherapy-induced antitumor immunity requires formyl peptide receptor 1. Science 350, 972-978 (2015).
T. Gibney, L. M. Weiner, M. B. Atkins, Predictive biomarkers for checkpoint inhibitor-based immunotherapy. Lancet Oncol. 17, e542-e551 (2016).
Y. Liou, P. Storz, Reactive oxygen species in cancer. Free Radic. Res. 44, 479-496 (2010).
Tang, Y. Wang, L. K. Chlewicki, Y. Zhang, J. Guo, W. Liang, J. Wang, X. Wang, Y. X. Fu, Facilitating T Cell Infiltration in Tumor Microenvironment Overcomes Resistance to PD-L1 Blockade. Cancer Cell 30, 500 (2016).
Sagiv-Barfi, H. E. K. Kohrt, D. K. Czerwinski, P. P. Ng, B. Y. Chang, R. Levy, Therapeutic antitumor immunity by checkpoint blockade is enhanced by ibrutinib, an inhibitor of both BTK and ITK. Proc. Natl. Acad. Sci. U.S.A. 112, E966-E972 (2015).
Segatto, S. Berton, M. Sonego, S. Massarut, T. Perin, E. Piccoli, A. Colombatti, A. Vecchione, G. Baldassarre, B. Belletti, Surgery-induced wound response promotes stem-like and tumor-initiating features of breast cancer cells, via STAT3 signaling. Oncotarget 5, 6267-6279 (2014).
A. Olson, C. McDonald-Hyman, S. C. Jameson, S. E. Hamilton, Effector-like CD8+ T cells in the memory population mediate potent protective immunity. Immunity 38, 1250-1260 (2013).
E. Rosenberg, J. Hoffman-Censits, T. Powles, M. S. van der Heijden, A. V. Balar, A. Necchi, N. Dawson, P. H. O'Donnell, A. Balmanoukian, Y. Loriot, S. Srinivas, M. M. Retz, P. Grivas, R. W. Joseph, M. D. Galsky, M. T. Fleming, D. P. Petrylak, J. L. Perez-Gracia, H. A. Burris, D. Castellano, C. Canil, J. Bellmunt, D. Bajorin, D. Nickles, R. Bourgon, G. M. Frampton, N. Cui, S. Mariathasan, O. Abidoye, G. D. Fine, R. Dreicer, Atezolizumab in patients with locally advanced and metastatic urothelial carcinoma who have progressed following treatment with platinum-based chemotherapy: a single-arm, multicentre, phase 2 trial. Lancet 387, 1909-1920 (2016).
Liu, D. Chen, G. D. Nie, Z. Dai, CD8+ CD122+ T-cells: a newly emerging regulator with central memory cell phenotypes. Front Immunol. 6, 494 (2015).
J. Naidoo, D. B. Page, B. T. Li, L. C. Connell, K. Schindler, M. E. Lacouture, M. A. Postow, J. D. Wolchok, Toxicities of the anti-PD-1 and anti-PD-L1 immune checkpoint antibodies. Ann. Oncol., mdv383 (2015).
J. Park, S. H. Wrzesinski, E. Stern, M. Look, J. Criscione, R. Ragheb, S. M. Jay, S. L. Demento, A. Agawu, P. L. Limon, Combination delivery of TGF-β inhibitor and IL-2 by nanoscale liposomal polymeric gels enhances tumour immunotherapy. Nat. Mater. 11, 895-905 (2012).
J. Vakkila, M. T. Lotze, Inflammation and necrosis promote tumour growth. Nat. Rev. Immunol. 4, 641-648 (2004).
Abiko, N. Matsumura, J. Hamanishi, N. Horikawa, R. Murakami, K. Yamaguchi, Y. Yoshioka, T. Baba, I. Konishi, M. Mandai, IFN-γ from lymphocytes induces PD-L1 expression and promotes progression of ovarian cancer. Br. J. Cancer 112, 1501-1509 (2015).
D. Moynihan, C. F. Opel, G. L. Szeto, A. Tzeng, E. F. Zhu, J. M. Engreitz, R. T. Williams, K. Rakhra, M. H. Zhang, A. M. Rothschilds, S. Kumari, K. L. Kelly, B. H. Kwan, W. Abraham, K. Hu, N. K. Mehta, M. J. Kauke, H. Suh, J. R. Cochran, D. A. Lauffenburger, K. D. Wittrup, D. J. Irvine, Eradication of large established tumors in mice by combination immunotherapy that engages innate and adaptive immune responses. Nat. Med. 22, 1402-1410 (2016).
K. Kagawa, S. Tomizawa, Exocytotic excretion of dextran sulfates from liver to bile. Jpn. J. Pharmacol. 30, 101-108 (1980).
E. Klevorn, R. M. Teague, Adapting Cancer Immunotherapy Models for the Real World. Trends Immunol. 37, 354-363 (2016).
Galluzzi, A. Buque, O. Kepp, L. Zitvogel, G. Kroemer, Immunogenic cell death in cancer and infectious disease. Nat. Rev. Immunol. 17, 97-111 (2017).
L. Gu, D. J. Mooney, Biomaterials and emerging anticancer therapeutics: engineering the microenvironment. Nat. Rev. Cancer 16, 56-66 (2016).

(56) References Cited

OTHER PUBLICATIONS

L. Z. Shi, T. Fu, B. Guan, J. Chen, J. M. Blando, J. P. Allison, L. Xiong, S. K. Subudhi, J. Gao, P. Sharma, Interdependent IL-7 and IFN-[gamma] signalling in T-cell controls tumour eradication by combined [alpha]-CTLA-4+[alpha]-PD-1 therapy. Nat. Comm. 7, (2016).
A. Kursunel, G. Esendagli, The untold story of IFN-gamma in cancer biology. Cytokine Growth Factor Rev. 31, 73-81 (2016).
Black, I. B. Barsoum, P. Truesdell, T. Cotechini, S. K. Macdonald-Goodfellow, M. Petroff, D. R. Siemens, M. Koti, A. W. Craig, C. H. Graham, Activation of the PD-1/PD-L1 immune checkpoint confers tumor cell chemoresistance associated with increased metastasis. Oncotarget 7, 10557-10567 (2016).
M. E. van Rossen, W. Sluiter, F. Bonthuis, H. Jeekel, R. L. Marquet, C. H. van Eijck, Scavenging of reactive oxygen species leads to diminished peritoneal tumor recurrence. Cancer Res. 60, 5625-5629 (2000).
M. Mandai, J. Hamanishi, K. Abiko, N. Matsumura, T. Baba, I. Konishi, Dual Faces of IFNgamma in Cancer Progression: A Role of PD-L1 Induction in the Determination of Pro- and Antitumor Immunity. Clin. Cancer Res. 22, 2329-2334 (2016).
A. Hotaling, L. Tang, D. J. Irvine, J. E. Babensee, Biomaterial Strategies for Immunomodulation. Annu. Rev. Biomed. Eng. 17, 317-349 (2015).
Antonio, M. L. Bonnelykke-Behrndtz, L. C. Ward, J. Collin, I. J. Christensen, T. Steiniche, H. Schmidt, Y. Feng, P. Martin, The wound inflammatory response exacerbates growth of pre-neoplastic cells and progression to cancer. EMBO J. 34, 2219-2236 (2015).
N. McGranahan, A. J. Furness, R. Rosenthal, S. Ramskov, R. Lyngaa, S. K. Saini, M. Jamal-Hanjani, G. A. Wilson, N. J. Birkbak, C. T. Hiley, T. B. Watkins, S. Shafi, N. Murugaesu, R. Mitter, A. U. Akarca, J. Linares, T. Marafioti, J. Y. Henry, E. M. Van Allen, D. Miao, B. Schilling, D. Schadendorf, L. A. Garraway, V. Makarov, N. A. Rizvi, A. Snyder, M. D. Hellmann, T. Merghoub, J. D. Wolchok, S. A. Shukla, C. J. Wu, K. S. Peggs, T. A. Chan, S. R. Hadrup, S. A. Quezada, C. Swanton, Clonal neoantigens elicit T cell immunoreactivity and sensitivity to immune checkpoint blockade. Science 351, 1463-1469 (2016).
N. Reznikov, J. A. M. Steele, P. Fratzl, M. M. Stevens, A materials science vision of extracellular matrix mineralization. Nat. Rev. Mater. 1, 16041 (2016).
N. S. Katheder, R. Khezri, F. O'Farrell, S. W. Schultz, A. Jain, M. M. Rahman, K. O. Schink, T. A. Theodossiou, T. Johansen, G. Juhasz, D. Bilder, A. Brech, H. Stenmark, T. E. Rusten, Microenvironmental autophagy promotes tumour growth. Nature 541, 417-420 (2017).
Sharma, J. P. Allison, Immune checkpoint targeting in cancer therapy: toward combination strategies with curative potential. Cell 161, 205-214 (2015).
Sharma, J. P. Allison, The future of immune checkpoint therapy. Science 348, 56-61 (2015).
Zhang, D. M. Su, M. Liang, J. Fu, Chemopreventive agents induce programmed death-1-ligand 1 (PD-L1) surface expression in breast cancer cells and promote PD-L1-mediated T cell apoptosis. Mol. Immunol. 45, 1470-1476 (2008).
A. Seder, P. A. Darrah, M. Roederer, T-cell quality in memory and protection: implications for vaccine design. Nat. Rev. Immunol. 8, 247-258 (2008).
Demicheli, M. Retsky, W. Hrushesky, M. Baum, I. Gukas, The effects of surgery on tumor growth: a century of investigations. Ann. Oncol., mdn386 (2008).
B. Stephan, A. M. Taber, I. Jileaeva, E. P. Pegues, C. L. Sentman, M. T. Stephan, Biopolymer implants enhance the efficacy of adoptive T-cell therapy. Nat. Biotechnol. 33, 97-101 (2015).
Bohm, A. Montfort, O. M. Pearce, J. Topping, P. Chakravarty, G. L. Everitt, A. Clear, J. R. McDermott, D. Ennis, T. Dowe, A. Fitzpatrick, E. C. Brockbank, A. C. Lawrence, A. Jeyarajah, A. Z. Faruqi, I. A. McNeish, N. Singh, M. Lockley, F. R. Balkwill, Neoadjuvant Chemotherapy Modulates the Immune Microenvironment in Metastases of Tubo-Ovarian High-Grade Serous Carcinoma. Clin. Cancer Res. 22, 3025-3036 (2016).
Kitano, K. Kataoka, Y. Koyama, T. Okano, Y. Sakurai, Glucose-responsive complex formation between poly (vinyl alcohol) and poly (N-vinyl-2-pyrrolidone) with pendent phenylboronic acid moieties. Makromol. Chem. Rapid Comm. 12, 227-233 (1991).
L. Topalian, J. M. Taube, R. A. Anders, D. M. Pardoll, Mechanism-driven biomarkers to guide immune checkpoint blockade in cancer therapy. Nat. Rev. Cancer 16, 275-287 (2016).
P. Arlauckas, C. S. Garris, R. H. Kohler, M. Kitaoka, M. F. Cuccarese, K. S. Yang, M. A. Miller, J. C. Carlson, G. J. Freeman, R. M. Anthony, In vivo imaging reveals a tumor-associated macrophage-mediated resistance pathway in anti-PD-1 therapy. Sci. Transl. Med. 9, eaal3604 (2017).
Doi, T. Okayama, T. Ishikawa, K. Oka, N. Sakamoto, T. Yasuda, Y. Naito, Y. Itoh. (AACR, 2015), Abstract 1330: The influence of anticancer agents and heat treatment on PD-L1 expression on human and murine pancreatic cancer cell lines.
Konno, K. Ishihara, Temporal and spatially controllable cell encapsulation using a water-soluble phospholipid polymer with phenylboronic acid moiety. Biomaterials 28, 1770-1777 (2007).
T. N. Schumacher, R. D. Schreiber, Neoantigens in cancer immunotherapy. Science 348, 69-74 (2015).
T. Walzer, C. Arpin, L. Beloeil, J. Marvel, Differential in vivo persistence of two subsets of memory phenotype CD8 T cells defined by CD44 and CD122 expression levels. J. Immunol. 168, 2704-2711 (2002).
T. Yamaoka, Y. Tabata, Y. Ikada, Comparison of Body Distribution of Poly (vinyl alcohol) with Other Water-soluble Polymers after Intravenous Administration. J. Pharm. Pharmacol. 47, 479-486 (1995).
A. Boussiotis, Molecular and Biochemical Aspects of the PD-1 Checkpoint Pathway. N. Engl. J. Med. 375, 1767-1778 (2016).
Ceelen, P. Pattyn, M. Mareel, Surgery, wound healing, and metastasis: Recent insights and clinical implications. Crit. Rev. Oncol. Hematol. 89, 16-26 (2014).
Zou, J. D. Wolchok, L. Chen, PD-L1 (B7-H1) and PD-1 pathway blockade for cancer therapy: Mechanisms, response biomarkers, and combinations. Sci. Transl. Med. 8, 328rv324 (2016).
Kaneo, S. Hashihama, A. Kakinoki, T. Tanaka, T. Nakano, Y. Ikeda, Pharmacokinetics and biodisposition of poly (vinyl alcohol) in rats and mice. Drug Metab. Pharmacokinet. 20, 435-442 (2005).
Zhang, S. Choksi, K. Chen, Y. Pobezinskaya, I. Linnoila, Z. G. Liu, ROS play a critical role in the differentiation of alternatively activated macrophages and the occurrence of tumor-associated macrophages. Cell Res. 23, 898-914 (2013).
Zoller, Mark J. "New recombinant DNA methodology for protein engineering." Current opinion in biotechnology 3.4 (1992): 348-354.
Jakobovits, Aya, et al. "Analysis of homozygous mutant chimeric mice: deletion of the immunoglobulin heavy-chain joining region blocks B-cell development and antibody production." Proceedings of the National Academy of Sciences 90.6 (1993): 2551-2555.
Jakobovits, Aya, et al. "Germ-line transmission and expression of a human-derived yeast artificial chromosome." Nature 362.6417 (1993): 255-258.
Brüggemann, Marianne, N. P. Davies, and I. R. Rosewell. "Designer mice: the production of human antibody repertoires in transgenic animals." The Year in immunology 7 (1993): 33-40.
Jones, Peter T., et al. "Replacing the complementarity-determining regions in a human antibody with those from a mouse." Nature 321.6069 (1986): 522-525.
Riechmann, Lutz, et al. "Reshaping human antibodies for therapy." Nature 332.6162 (1988): 323-327.
Pluckthum, Andreas. "Antibody engineering." Current Opinion in Biotech (1991), 2:238-246.
Verhoeyen, Martine, Cesar Milstein, and Greg Winter. "Reshaping human antibodies: grafting an antilysozyme activity." Science 239. 4847 (1988): 1534-1536.
Senter, Peter D., et al. "Generation of 5-fluorouracil from 5-fluorocytosine by monoclonal antibody-cytosine deaminase conjugates." Bioconjugate chemistry 2.6 (1991): 447-451.

(56) References Cited

OTHER PUBLICATIONS

Bagshawe, K. D. "Towards generating cytotoxic agents at cancer sites. The First Bagshawe Lecture." Br. J. Cancer 60 (1989): 275-281.
Bagshawe, et al., Br. J. Cancer, 58:700-703, (1988).
Senter, et al., Bioconjugate Chem., 4:3-9, (1993).
Battelli, et al., Cancer Immunol. Immunother., 35:421-425, (1992).
Pietersz and McKenzie, Immunolog. Reviews, 129:57-80, (1992).
Roffler, et al., Biochem. Pharmacol, 42:2062-2065, (1991).
Litzinger and Huang, Biochimica et Biophysica Acta, 1104:179-187, (1992).
Hughes et al., Cancer Research, 49:6214-6220, (1989).
Brown and Greene, DNA and Cell Biology 10:6, 399-409 (1991).
Ferrone et al., eds., Noges Publications, Park Ridge, N.J., (1985) ch. 22 and pp. 303-335.
Smith et al., Antibodies in Human Diagnosis and Therapy, Haber et al., eds., Raven Press, New York (1977) pp. 365-389.
International Preliminary Report on Patentability issued for Application No. PCT/US2018/065382, dated June 25, 2020.
Extended European Search Report issued in corresponding Application No. EP 18887991.0, dated Oct. 22, 2021, 8 pages.
Zhao, Kejian, Pocket Booklet for New Specific Medicine, 2004, paragraph 2, p. 291. [English translation].
Chen, Di, Regulating the Tumor Microenvironment of Pancreatic Cancer by Nanoimmunosystem and Its Synergistically Mechanism in Promoted Chemoradiotherapy, published on Sep. 26, 2017. [English translation].
Gupta, Mukesh K. et al., Cell Protective, ABC Triblock Polymer-Based Thermoresponsive Hydrogels with ROS-Triggered Degradation and Drug Release (2014) J. Amer. Chem. Soc., vol. 136, No. 42X, pp. 14896-14902.
Zuo, Qiaozhu et al., "Progress of CTLA-4 and PD-1 signaling pathways in immunotherapy for human solid cancers," Chinese Bulletin of Life Sciences, vol. 29, No. 8, pp. 713-721.
Decaup, Emilie et al., Focal Adhesion Kinase: A promising therapeutic target in pancreatic adenocarcinoma, Clinics and Research in Hepatology and Gastroenterology, Dec. 31, 2016.

* cited by examiner

FIG. 1A, FIG. 1B, FIG. 1C, FIG. 1D, FIG. 1E, and FIG. 1F

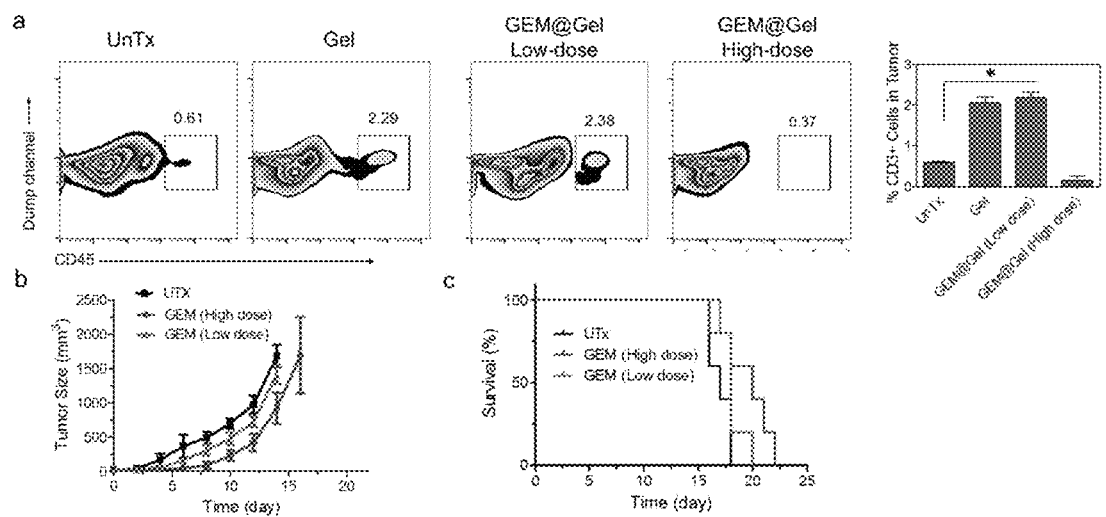
FIG. 5A, FIG. 5B, and FIG. 5C

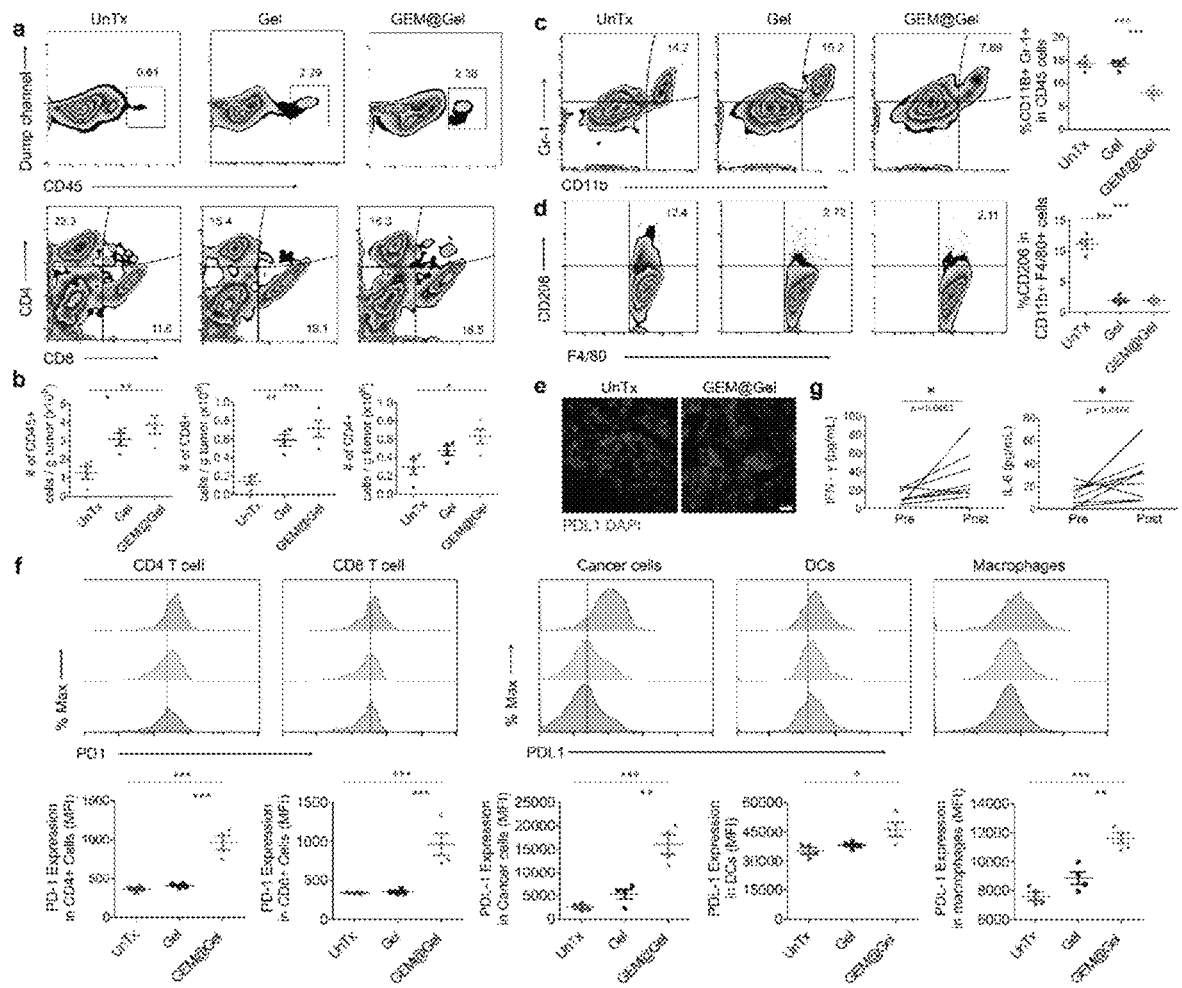
FIG. 6A, FIG. 6B, FIG. 6C, FIG. 6D, FIG. 6E, FIG. 6F, and FIG. 6G

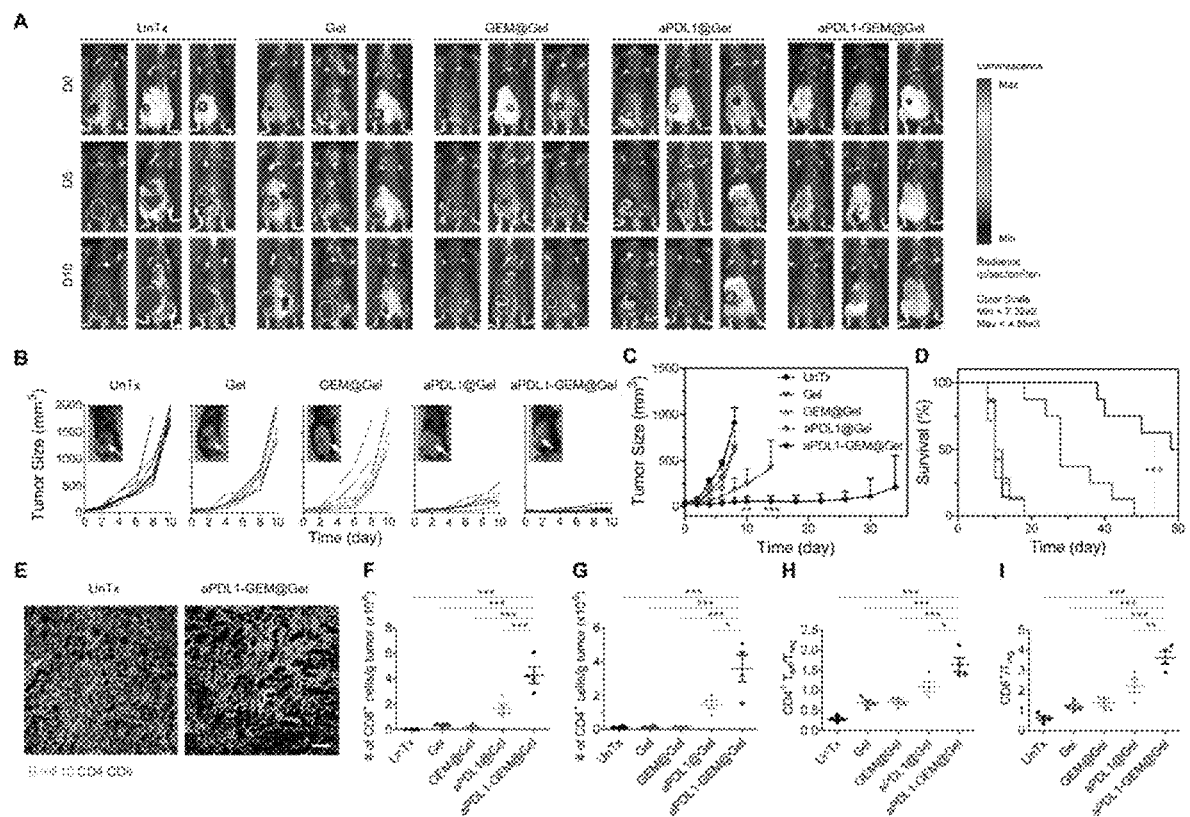
FIG. 8A, FIG. 8B, FIG. 8C, FIG. 8D, FIG. 8E, FIG. 8F, FIG. 8G, FIG. 8H, and FIG. 8I FIG. 10A, FIG. 10B, FIG. 10C, FIG. 10D, FIG. 10E, FIG. 10F, FIG. 10G, FIG. 10H, and FIG. 10I FIG. 11A, FIG. 11B, FIG. 11C, FIG. 11D, FIG. 11E, FIG. 11F, and FIG. 11G

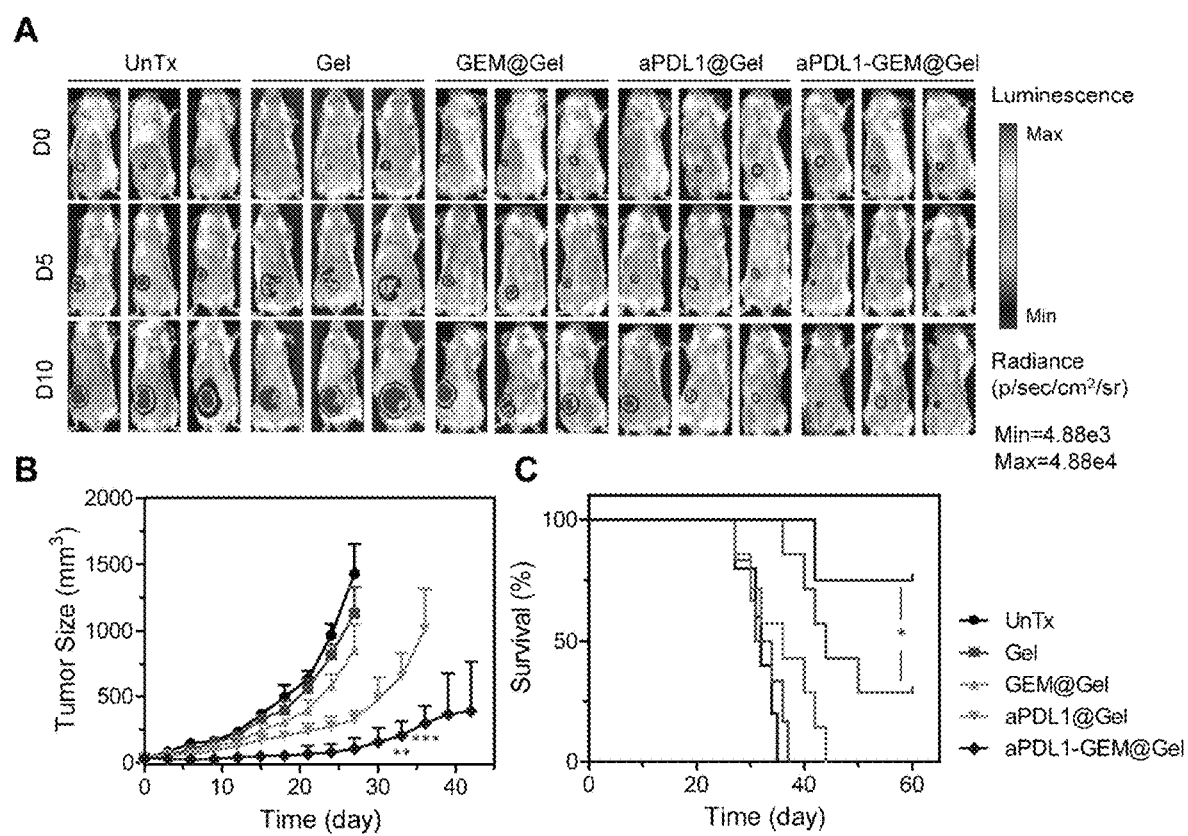
FIG. 13A, FIG. 13B, and FIG. 13C

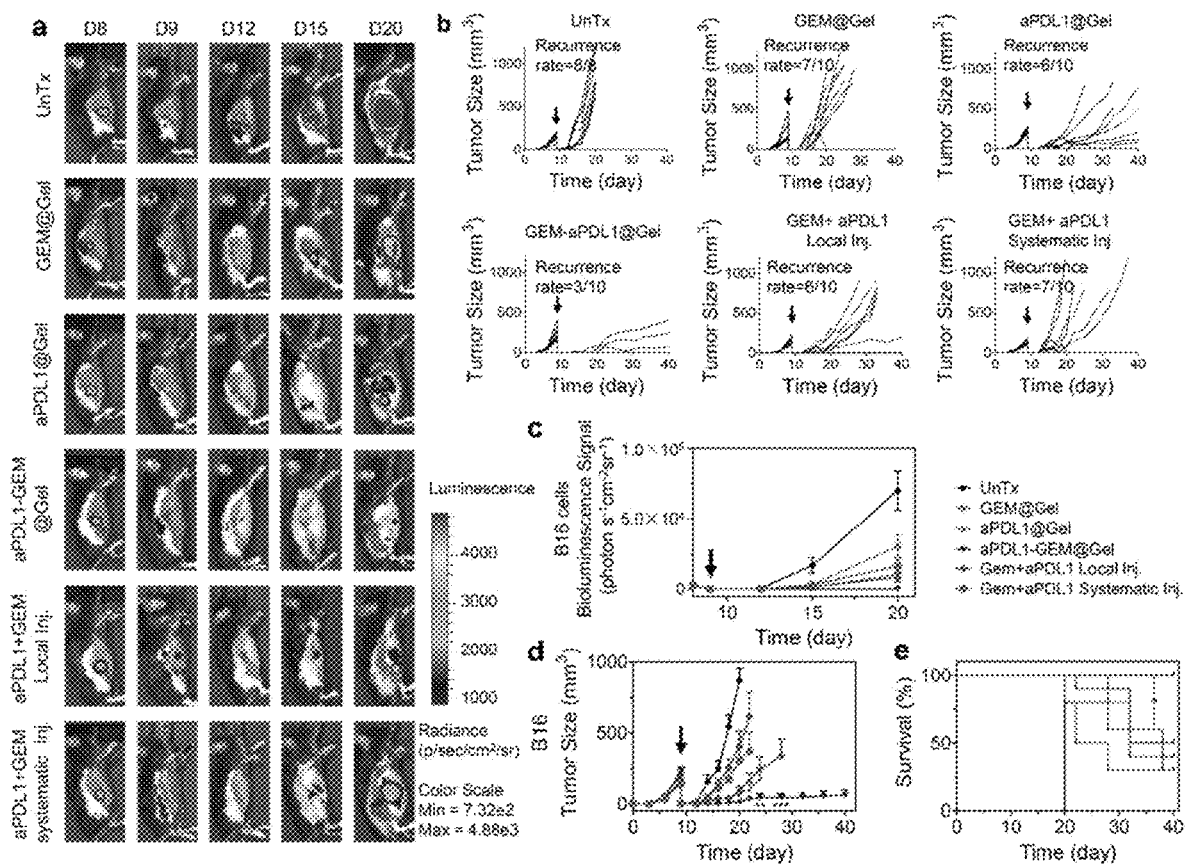
FIG. 14A, FIG. 14B, FIG. 14C, FIG. 14D, and FIG. 14E

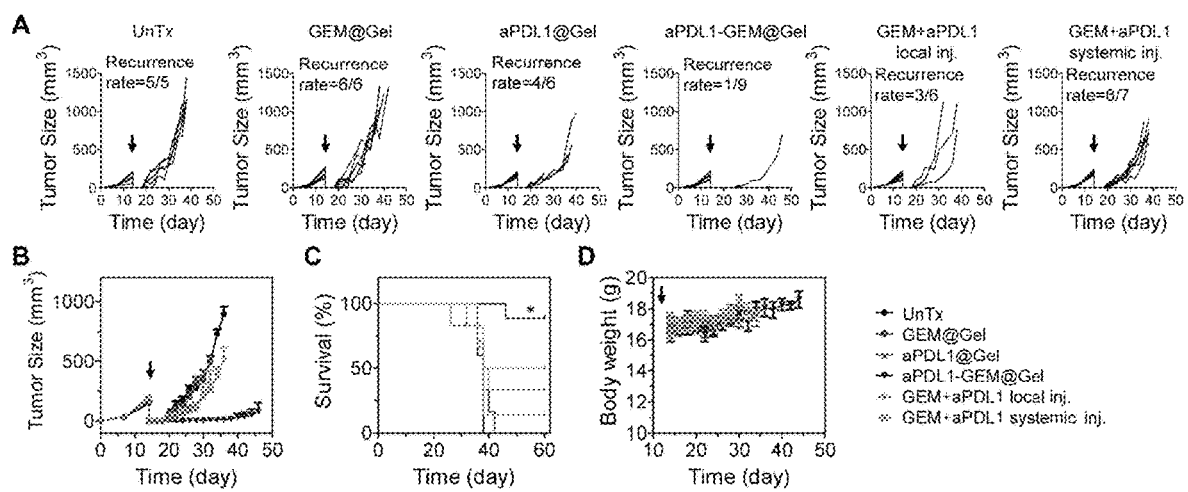
FIG. 15A, FIG. 15B, FIG. 15C, and FIG. 15D

COMPOSITIONS COMPRISING CHEMOTHERAPEUTIC AGENTS AND CHECKPOINT INHIBITORS AND METHODS OF USE

This is a national stage application filed under 35 U.S.C. § 371 of PCT/US2018/065382, filed on Dec. 13, 2018, which claims the benefit of U.S. Provisional Application No. 62/598,254, filed on Dec. 13, 2017 which are incorporated herein by reference in their entireties. This invention was made with government support under Grant No. TR001111 awarded by National Institutes of Health. The government has certain rights in the invention.

I. BACKGROUND

Immune checkpoint blockade (ICB) targeting the programmed death-1/programmed death-ligand 1 (PD-1/PD-L1) pathway induces remarkable clinical responses in various malignancies, including melanoma, non-small cell lung, kidney, head and neck and bladder cancers. However, only patients with immunogenic tumors characterized by high neoantigen burden, pre-infiltration of effector T cells and expression of PD-L1 seem to achieve durable clinical responses after the administration of ICB. Moreover, clinical application of ICB has also been associated with various side effects in normal organs. Based on these studies, strategies aimed at promoting an immunogenic tumor phenotype, increasing ICB response, and avoiding severe side effects remain a central theme in the field of cancer immunotherapy.

II. SUMMARY

Disclosed are methods and compositions related to bioresponsive hydrogel matrixes comprising a chemotherapeutic agent and a blockade inhibitor.

Disclosed herein are methods of treating/inhibiting/reducing a non-immunogenic cancer in a subject or inducing blockade inhibitor susceptibility (such as, for example, PD-1/PD-L1, CTLA-4/B7-1/2, and/or CD47/SIRPα inhibitor susceptibility) in a tumor in a subject with a cancer, said methods comprising administering to the subject a hydrogel matrix comprising a chemotherapeutic agent (including, but not limited to gemcitabine) and a blockade inhibitor (including, but not limited to a PD-1/PD-L1 blockade inhibitor, such as, for example nivolumab, pembrolizumab, pidilizumab, atezolizumab, avelumab, durvalumab, and BMS-936559; a CTLA-4/B7-1/2 inhibitor such as, for example, Ipilimumab; and/or a CD47/SIRPα inhibitor such as, for example Hu5F9-G4, CV1, B6H12, 2D3, CC-90002, and TTI-621).

Also disclosed are methods of any preceding aspect, wherein the hydrogel matrix comprises a bioresponsive scaffold releases the chemotherapeutic and blockade inhibitor (such as, for example, PD-1/PD-L1, CTLA-4/B7-1/2, and/or CD47/SIRPα inhibitors) into the tumor microenvironment upon exposure to factors within the microenvironment.

In one aspect, disclosed herein are methods of any preceding aspect, wherein the hydrogel matrix comprises a reactive oxygen species (ROS) degradable hydrogel.

Also disclosed are methods of any preceding aspect, wherein the hydrogel releases the chemotherapeutic and blockade inhibitor (such as, for example, PD-1/PD-L1, CTLA-4/B7-1/2, and/or CD47/SIRPα inhibitors) into the tumor microenvironment for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

In one aspect, disclosed herein are methods of any preceding aspect, wherein the chemotherapeutic and blockade inhibitor (such as, for example, PD-1/PD-L1, CTLA-4/B7-1/2, and/or CD47/SIRPα inhibitors) are released from the hydrogel at the same rate or at different rates.

Also disclosed are methods of any preceding aspect, wherein the cancer a cancer with low PD-L1 expression or a non-immunogenic cancer selected from the group consisting of melanoma, non-small cell lung carcinoma, renal cancer, head and neck cancer, and bladder cancer.

Also disclosed herein are bioresponsive hydrogel matrixes comprising a chemotherapeutic agent (including, but not limited to gemcitabine) and a blockade inhibitor (including, but not limited to a PD-1/PD-L1 blockade inhibitor, such as, for example nivolumab, pembrolizumab, pidilizumab, atezolizumab, avelumab, durvalumab, and BMS-936559; a CTLA-4/B7-1/2 inhibitor such as, for example, Ipilimumab; and/or a CD47/SIRPα inhibitor such as, for example Hu5F9-G4, CV1, B6H12, 2D3, CC-90002, and TTI-621).

In one aspect, disclosed herein are bioresponsive hydrogel matrix of any preceding aspect, wherein the hydrogel matrix comprises a reactive oxygen species (ROS) degradable hydrogel.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, 1C, 1D, 1E, and 1F show a schematic and characterization of in situ formed reactive oxygen species (ROS)-responsive PVA-TSPBA scaffold. FIG. 1A shows a schematic of synergistic chemoimmunotherapy using an ROS-degradable hydrogel scaffold to deliver gemcitabine (GEM) and anti-PD-L1 (aPDL1) into the tumor microenvironment (TME). FIG. 1B shows representative Cryo-SEM image of gel scaffold loaded with GEM and aPDL1. Scale bar, 0.5 μm. Inset: a zoom-in image of the scaffold. Scale bar, 0.1 μm. FIG. 1C shows representative fluorescent image of cryosection of hydrogels in which FITC was used as a fluorescent surrogate for GEM (green) and aPDL1 was labeled with Cy5.5 (red). Scale bar, 25 μm. FIG. 1D shows morphology changes of hydrogels in 1×PBS with and without $H_2O_2$ (0.1 mM) during 7 days. FIGS. 1E and 1F show cumulative release profiles of GEM (1e) and aPDL1 (1f) from hydrogels when incubated with PBS with or without $H_2O_2$ (1 mM).

Figure 4:
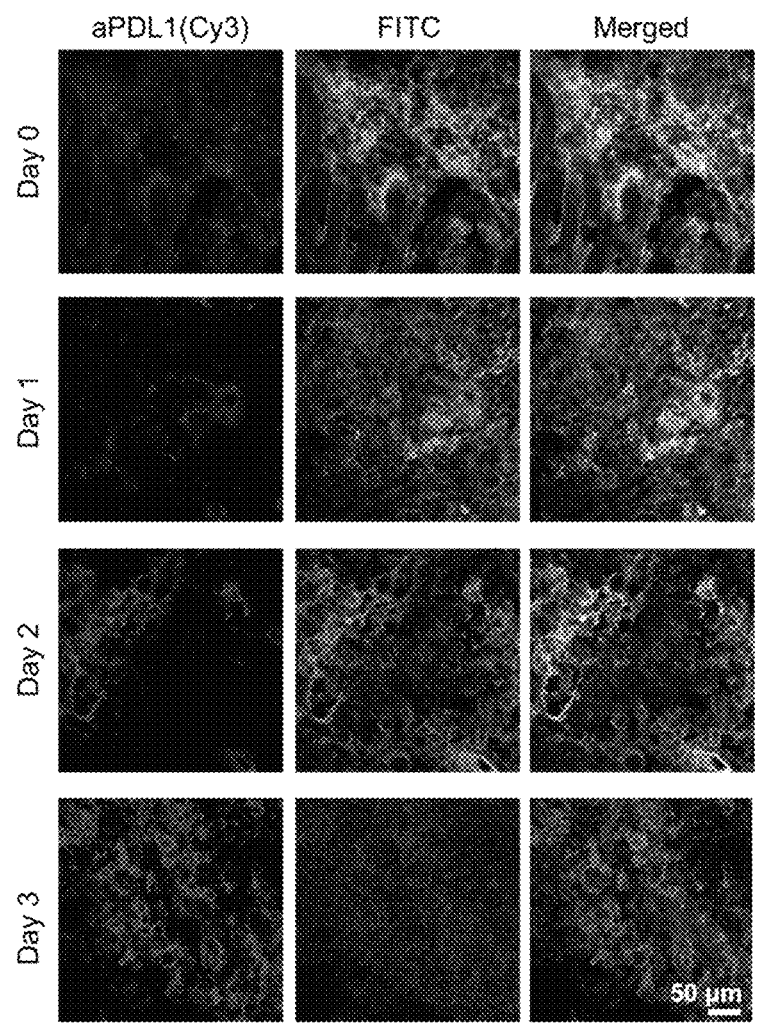

FIG. 4 shows confocal immunofluorescence images of B16 tumors collected after aPDL1 and GEM loaded gel injection at different time points (15 min (0 day), 1, 2, and 3 days after the injection) based on at least triplicate measurements. Red and green fluorescence indicates aPDL1 (Cy3-goat anti-rat IgG) and FITC (fluorescent surrogate for GEM), respectively. Note: the antibody was released constantly, with enhanced retention in the tumor once PDL1 was upregulated by GEM.

FIGS. 5A, 5B, and 5C show low-dose GEM@Gel enhanced T cell infiltration in tumors. FIG. 5A shows representative flow cytometric analysis showing the frequency of CD3+ T cells within tumors collected after the indicated treatments. The error bars represent standard error of the mean (SEM) (n=3). FIG. 5B shows tumor growth in mice receiving the indicated treatments (n=5). Growth curves represent mean±SEM. FIG. 5C shows Kaplan-Meier survival-curves of mice receiving the indicated treatments (n=5). Statistical significance was calculated by one-way ANOVA using the Tukey post-test. P value: *, P<0.05; , P<0.01; *P<0.005.

FIGS. 6A, 6B, 6C, 6D, 6E, 6F, and 6G show GEM@Gel implantation elicits immunogenic tumor phenotypes. B16F10 tumors harvested from mice implanted with hydrogels or GEM@ hydrogels were analyzed by flow cytometry two days after treatment. FIG. 6A shows representative flow cytometric analysis of T cell infiltration within the tumor and (6b) corresponding quantification results. FIG. 6C shows representative flow cytometric analysis images (left) and the corresponding quantification (right) of MDSCs (CD11b+Gr-1+) gating on CD45+ cells. FIG. 6D shows representative flow cytometric analysis images (left) and the corresponding quantification (right) of M2-macrophages (CD206+) in F4/80+CD11b+CD45+ cells. FIG. 6E shows confocal immunofluorescence images of B16F10 tumor with (upper) or without (lower) GEM@ hydrogels treatment. Red and blue colors represent aPDL1 signals from Cy3 conjugated anti-PD-L1 antibody and nucleus from DAPI, respectively. Scale bar, 20 µm. FIG. 6F shows PD-L1 expression of tumor cells and tumor-infiltrating lymphocytes after hydrogels or GEM@ hydrogels treatment and the corresponding quantification of PD-L1 mean intensity. FIG. 6G shows systemic IL6 and IFN-γ levels before and after GEM@ hydrogels treatment. The error bars are based on the standard error of the mean (s.e.m.). Statistical significance was calculated by one-way ANOVA using the Tukey post-test. P value: *, P<0.05; , P<0.01; *P<0.005.

Figures 7A, 7B:
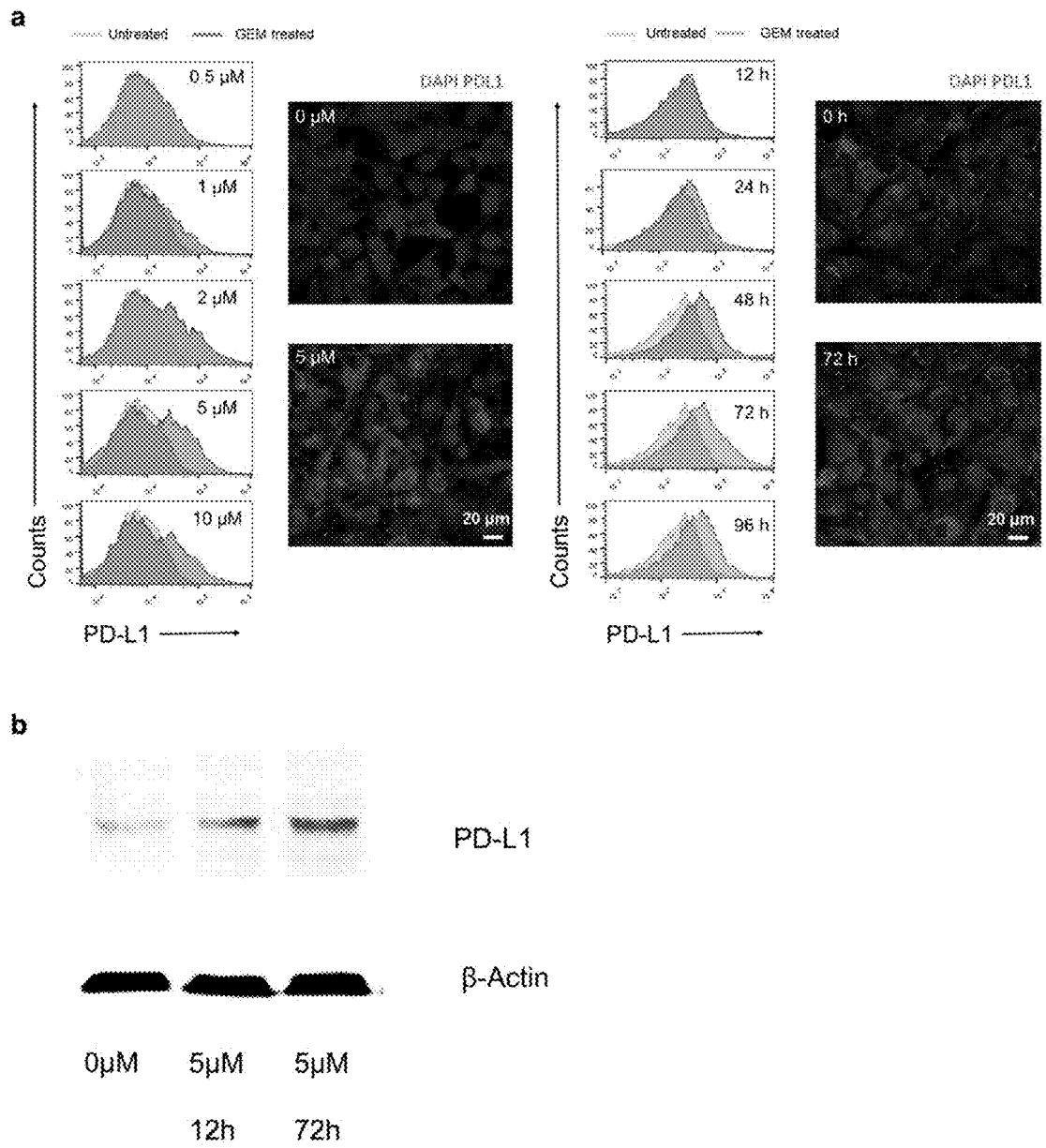

FIGS. 7A and 7B show the effects of GEM to cancer cells in vitro. FIG. 7A shows treatment of B16F10 cells with GEM (5 µM) caused significant PD-L1 upregulation on surviving cells within 24 hours as assessed by flow cytometry and immunofluorescence based on at least triplicate measurements. FIG. 7B shows western blot also showed PD-L1 upregulation.

FIGS. 8A, 8B, 8C, 8D, 8E, 8F, 8G, 8H, and 8I show that local chemoimmunotherapy controls B16F10 melanoma growth in vivo. (8a) In vivo bioluminescence imaging of the B16F10 tumor in treated and control groups. Shown were 4-5 representative mice per treatment group. (8b-8c) Individual (8b) and average (8c) tumor growth kinetics in control and treated groups (treatment started at day 0). Inset: Representative mice photographs 2 weeks after treatment. White arrows indicate the tumor. (8d) Survival curves for the treated and control mice. Growth curves represent mean±SEM; Growth curves were stopped when the first animal of the corresponding group died; Kaplan-Meier survival-curves (n=7-10). *P<0.05; P<0.01; *P<0.001. (8e) Immunofluorescence of tumors showing CD4+ and CD8+ T cell infiltration. Scale bar, 100 pin. (8f-8g) Absolute number of the CD8+(80 and CD4+ T cells (g) per gram of the tumor upon various treatments. (8h-8i) Ratios of the tumor-infiltrating CD8+ T cells (8h) and CD4+ T cells (8i) over regulatory T cells in the tumors upon various treatments. The error bars represent standard error of the mean (s.e.m.). Statistical significance was calculated by one-way ANOVA using the Tukey post-test. P value: *, P<0.05; , P<0.01; *P<0.005.

Figure 9:
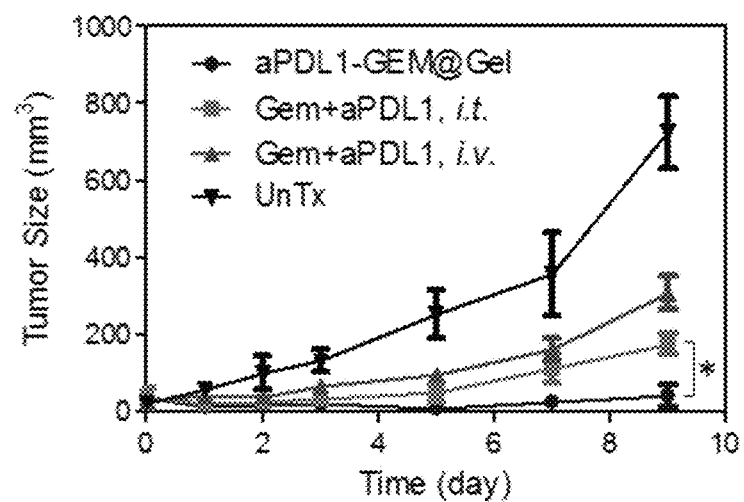

FIG. 9 shows tumor growth in mice treated with free drugs (n=6). The error bars represent standard error of the mean. Statistical significance was calculated by one-way ANOVA using the Tukey post-test. P value: *P<0.05.

Figure 10:
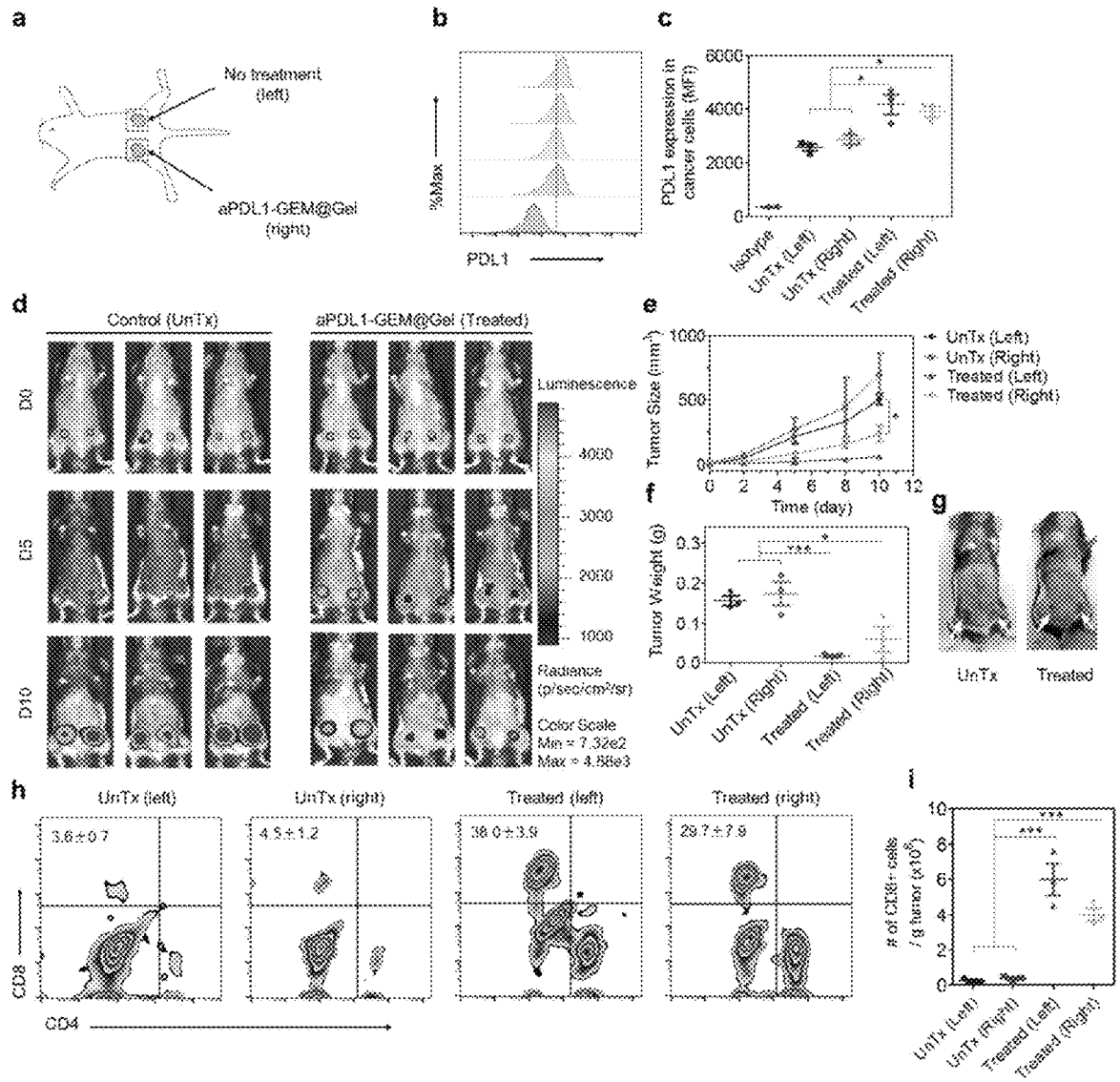

FIGS. 10A, 10B, 10C, 10D, 10E, 10F, 10G, 10H, and 10I show that local chemoimmunotherapy induces systemic anticancer immune response. FIG. 10A shows mice were inoculated with tumor cells in the right and left flank. Control mice were untreated, while treated mice were implanted with hydrogels only on the left flank. FIG. 10B shows PD-L1 expression of cancer cells collected from tumor site of the control and treated mice, and (10c) corresponding quantification of PD-L1 mean intensity (n=3). (10d) In vivo bioluminescence imaging of B16F10 tumors in response to local aPDL1-GEM@ hydrogels treatment. (10e) Left and right tumor growth curves and (10f) weight at Day 10 in untreated and treated mice. (10g) Representative mice photographs at day 10 after treatment. White arrows indicate the tumors. (10h) Percentages of CD4+ and CD8+ T cells, and representative dot plots in tumor of control and treated mice, and (10i) absolute number of the CD8+ cells per gram of tumors. The error bars indicate standard error of the mean (s.e.m.). Statistical significance was calculated by one-way ANOVA using the Tukey post-test. P value: *, P<0.05; , P<0.01; *P<0.005.

FIGS. 11A, 11B, 11C, 11D, 11E, 11F, and 11G show that local chemoimmunotherapy induces T cell memory response. (11a) Splenocytes isolated from tumor-bearing control and treated mice were analyzed for the presence of CD8+CD44+CD122+ and CD4+CD44+CD122+ TCM cells. (11b-11c) Corresponding quantification of TCM in splenocytes. (11d) In vivo bioluminescence imaging of mice after re-challenging with intravenous injection of B16F10 cancer cells. (11e) Representative lung photographs (day 10) and (11f) H&E staining of lung collected from control (naïve) and treated (cured) mice after re-challenging. The blue arrows indicated the metastatic tumors in the lung. Scale bar, 100 µm. (11g) Survival curves for naïve and cured mice. Shown are 5 mice for each group for the survival study. The error bars illustrate the standard error of the mean (s.e.m.). Statistical significance was calculated by one-way ANOVA using the Tukey post-test. P value: *, P<0.05; **, P<0.01.

Figure 12:
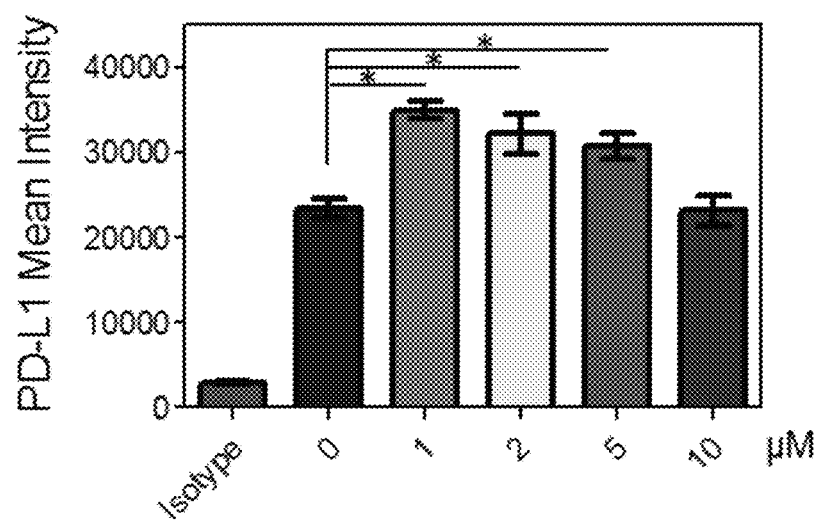

FIG. 12 shows the effects of GEM in 4T1 cells in vitro. Treatment of 4T1 cells with various concentrations (0, 1, 2, 5, 10 µM) of GEM for 48 hours resulted in PD-L1 upregulation on remaining live cells as assessed by flow cytometry. The data are shown as mean±SD. Error bars are based on at least triplicate measurements. P value: *, P<0.05.

FIGS. 13A, 13B, and 13C show that local chemoimmunotherapy controls the low-immunogenic 4T1 carcinoma tumor. FIG. 13A shows In vivo bioluminescence imaging of the 4T1 tumor growth in control and treated mice. FIG. 13B shows tumor growth kinetics in control and treated mice. FIG. 13C shows survival curves for control and treated mice. Growth curves represent mean±SEM; Growth curves were stopped when the first animal of the corresponding group was euthanized; Kaplan-Meier survival-curves (n=7-10). Growth curves represent mean±SEM. Statistical significance was calculated by one-way ANOVA using the Tukey post-test. *P<0.05; P<0.01; *P<0.001.

FIGS. 14A, 14B, 14C, 14D, and 14E show that gel scaffold for preventing post-surgical recurrence of tumors. FIG. 14A shows In vivo bioluminescence imaging of the B16F10 tumor growth in C57B6 mice after various treatments as indicated. (14B, 14C, and 14D) Individual (14b) and average quantitative bioluminescence signals of tumor (14c), and tumor growth kinetics (14d) in control and treated groups. Black arrows indicate the day of the surgery (day 9). FIG. 14E shows survival curves for different treatments. The error bars show standard error of the mean (s.e.m.). Growth curves were stopped when the first animal of the corresponding group was euthanized; Kaplan-Meier survival-curves (n=7-10). Growth curves represent mean±SEM. Statistical significance was calculated by one-way ANOVA using the Tukey post-test. *P<0.05; P<0.01; *P<0.001.

FIGS. 15A, 15B, 15C, and 15D show the gel scaffold for preventing post-surgical recurrence of 4T1 tumors. (15a) Individual and (15b) average tumor growth kinetics in control and treated groups receiving the indicated treatments. FIG. 15C shows survival curves for different treatments. FIG. 15D shows measurements of body weight of control and treated mice. The error bars show standard error of the mean (s.e.m.); Growth curves were stopped when the first animal of the corresponding group died; Kaplan-Meier survival-curves (n=5-9, as indicated in the figure). *P<0.05. Black arrows indicate the day of the surgery (day 14).

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular hydrogel matrix comprising a chemotherapeutic agent and a blockade inhibitor is disclosed and discussed and a number of modifications that can be made to a number of molecules including the hydrogel matrix comprising a chemotherapeutic agent and a blockade inhibitor are discussed, specifically contemplated is each and every combination and permutation of hydrogel matrix comprising a chemotherapeutic agent and a blockade inhibitor and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Prior chemotherapy enhances the therapeutic outcome of immunotherapy, which also reversed chemoresistance after prolonged chemotherapy. While some chemotherapeutic drugs have modest activity when used as single treatment, their combination with immunotherapy can result in enhanced anticancer effects. These observations pave the rationale to assume that some chemotherapy drugs can be used to promote an immunogenic tumor phenotype. On the other hand, engineered delivery vehicles or scaffolds are increasingly considered promising tools for transporting immunotherapeutics, with decreased systemic toxicities. However, the regulated release of payloads and the kinetics of the degradation of the supporting matrix upon in vivo administration are aspects particularly relevant for the treatment efficacy.

Figure 1:
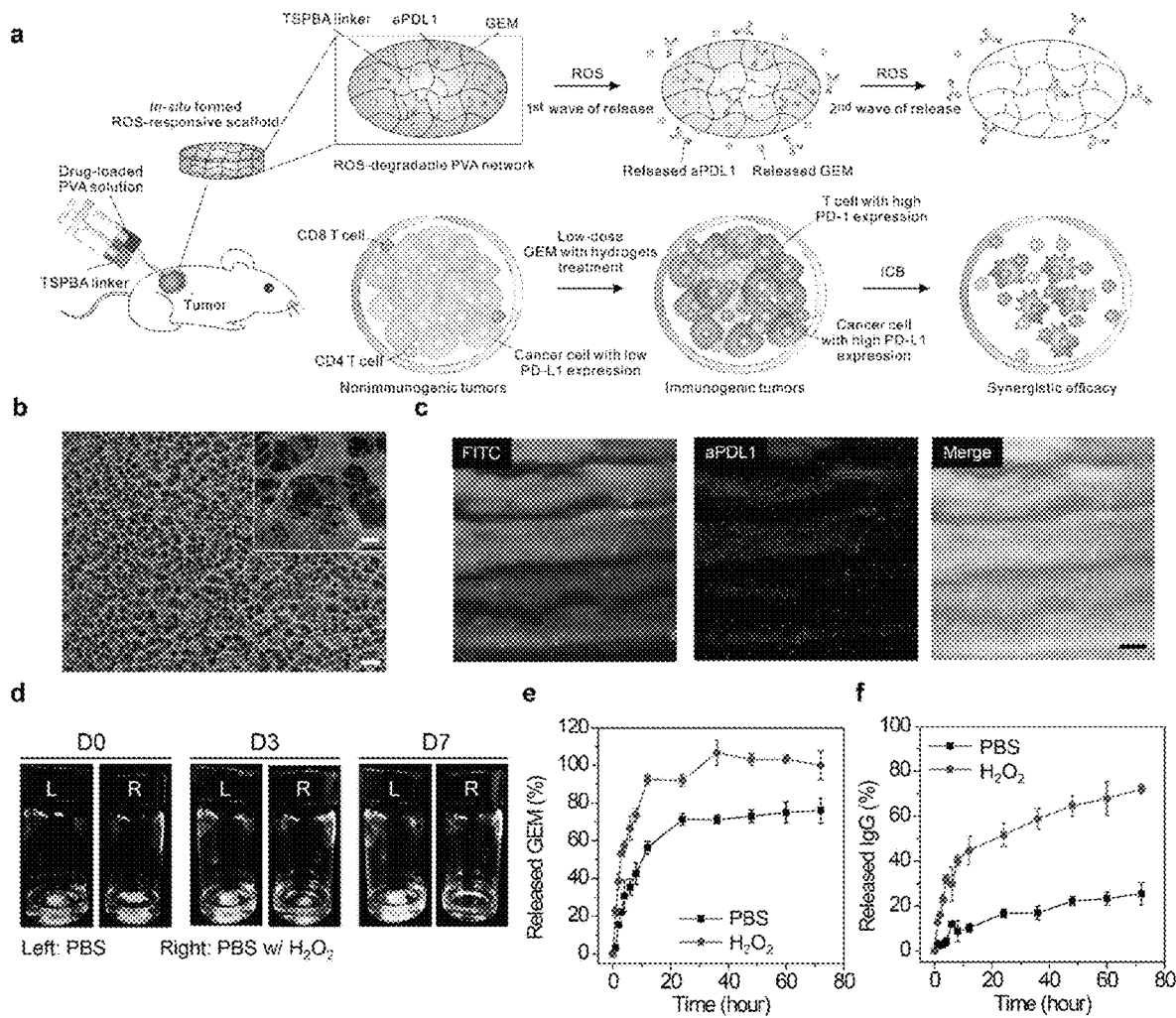

Herein, a bioresponsive scaffold was generated that was suitable for localized chemo-immunotherapy in which gemcitabine (GEM) induces an immunogenic tumor phenotype and ICB promotes subsequent therapeutic immune response (FIG. 1a). It was hypothesized that injectable ROS-responsive hydrogels can be utilized to load and release therapeutics upon implantation into the tumor site due to highly abundant ROS, which promoted cancer development and progression, expressed within the tumor microenvironment (TME). Here, a clinically relevant prototype of ROS-degradable hydrogel scaffold promotes an immunogenic tumor phenotype via local GEM delivery and antitumor responses through local release of aPD-L1 in the B16F10 melanoma and 4T1 breast tumor (relative low-immunogenic)-bearing mouse models. Therapeutic advantage of this chemo-immunotherapy is also demonstrated by the prevention of tumor recurrence after primary resection. Accordingly, in one aspect, disclosed herein are hydrogel matrixes comprising a chemotherapeutic agent and a blockade inhibitor.

It is understood and herein contemplated that the chemotherapeutic used in the disclosed hydrogel matrixes can comprise any chemotherapeutic known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN- TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Iniquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Margibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EP- OCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Accordingly, in one aspect, disclosed herein are hydrogel matrixes comprising a chemotherapeutic agent and a blockade inhibitor; wherein the chemotherapeutic agent is gemcitabine.

In one aspect, the blockade inhibitor that can be used in the disclosed hydrogel matrixes can be any inhibitor of an immune checkpoint such as for example, a PD-1/PD-L1 blockade inhibitor, a CTLA-4/B7-1/2 blockade inhibitor (such as for example, Ipilimumab), and CD47/Signal Regulator Protein alpha (SIRPα) blockade inhibitor (such as for example, Hu5F9-G4, CV1, B6H12, 2D3, CC-90002, and/or TTI-621). Examples, of PD-1/PD-L1 blockade inhibitors for use in the disclosed hydrogel matrixes can include any PD-1/PD-L1 blockade inhibitor known in the art, including, but not limited to nivolumab, pembrolizumab, pidilizumab, atezolizumab, avelumab, durvalumab, and BMS-936559).

Thus, in one aspect, disclosed herein are hydrogel matrixes comprising a chemotherapeutic agent and a blockade inhibitor; wherein the blockade inhibitor is a PD-1/PD-L1 blockade inhibitor such as, for example, nivolumab, pembrolizumab, pidilizumab, atezolizumab, avelumab, durvalumab, and BMS-936559; a CTLA-4/B7-1/2 inhibitor such as, for example, Ipilimumab; and/or a CD47/SIRPα inhibitor such as, for example Hu5F9-G4, CV1, B6H12, 2D3, CC-90002, and TTI-621. It is understood and herein contemplated that the hydrogel matrix can be designed to incorporate 1, 2, 3, 4, 5, 6, 7, 8, 9, 10, 11, 12, 13, 14, or 15 blockade inhibitors simultaneously.

It is understood and herein contemplated that the hydrogel matrix can be designed to be bioresponsive to the microenvironment of the tumor and release the chemotherapeutic agent and/or blockade inhibitor (such as, for example, PD-1/PD-L1, CTLA-4/B7-1/2, and/or CD47/SIRPα inhibitors) upon exposure to factors within the microenvironment such as, for example reactive oxygen species, including, but not limited to peroxides (for example hydrogen peroxide), superoxide, hydroxyl radical, and singlet oxygen; the presence of acidity; redox potential (glutathione (GSH)); specific tumor-associated enzymes; hypoxia; and adenosine-5'-triphosphate (ATP). Thus, in one aspect, disclosed herein are bioresponsive hydrogel matrix of any preceding aspect, wherein the hydrogel matrix comprises a reactive oxygen species (ROS) degradable hydrogel.

1. Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with PD-1, PD-L1, CTLA-4, B7-1/2, CD47, and/or SIRPα such that PD-1 is inhibited from interacting with PD-L1, CTLA-4 is inhibited from interacting with B7-1/2, or CD47 is inhibited from interacting with SIRPα. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, and fragments, such as F(ab')2, Fab', Fab, Fv, scFv, and the like, including hybrid fragments. Thus, fragments of the antibodies that retain the ability to bind their specific antigens are provided. For example, fragments of antibodies which maintain PD-1, PD-L1, CTLA-4, B7-1/2, CD47, and/or SIRPα binding activity are included within the meaning of the term "antibody or fragment thereof" Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an sFv, Fv, Fab, Fab', F(ab')2, or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The broadly neutralizing anti-PD-1, PD-L1, CTLA-4, B7-1/2, CD47, and/or SIRPα antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

2. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, P A 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice.

Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

3. Method of Treating Cancer and Inducing Blockade Inhibitor Susceptibility in a Tumor The disclosed compositions can be used to treat any disease where uncontrolled cellular proliferation occurs such as cancers. Accordingly, in one aspect, disclosed herein are methods of treating/inhibiting/reducing a non-immunogenic cancer in a subject and/or inducing blockade inhibitor susceptibility (such as, for example, PD-1/PD-L1, CTLA-4/B7-1/2, and/or CD47/SIRPα inhibitor susceptibility) in a tumor in a subject with a cancer, said methods comprising administering to the subject a hydrogel matrix comprising a chemotherapeutic agent and a blockade inhibitor.

In one aspect, the hydrogel matrix used in the disclosed methods of treating/inhibiting/reducing a non-immunogenic cancer in a subject and/or inducing blockade inhibitor susceptibility (such as, for example, PD-1/PD-L1, CTLA-4/B7-1/2, and/or CD47/SIRPα inhibitor susceptibility) in a tumor in a subject with a cancer comprises a chemotherapeutic agent. The chemotherapeutic used in the disclosed methods can comprise any chemotherapeutic known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane),Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besonsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Thus, in one aspect, disclosed herein are methods of treating a non-immunogenic cancer in a subject and/or inducing PD-1/PD-L1 blockade inhibitor susceptibility in a tumor in a subject with a cancer, said methods comprising administering to the subject a hydrogel matrix comprising a chemotherapeutic agent and a blockade inhibitor; wherein the chemotherapeutic agent is gemcitabine.

In one aspect, the hydrogel matrix used in the disclosed methods of treating/inhibiting/reducing a non-immunogenic cancer in a subject and/or inducing blockade inhibitor susceptibility (such as, for example, PD-1/PD-L1, CTLA-4/B7-1/2, and/or CD47/SIRPα inhibitor susceptibility) in a tumor in a subject with a cancer comprises a blockade inhibitor. In one aspect, the blockade inhibitor can be a PD-1/PD-L1 blockade inhibitor, a CTLA-4/B7-1/2 blockade inhibitor (such as for example, Ipilimumab), and CD47/Signal Regulator Protein alpha (SIRPα) blockade inhibitor (such as for example, Hu5F9-G4, CV1, B6H12, 2D3, CC-90002, and/or TTI-621). Examples, of PD-1/PD-L1 blockade inhibitors for use in the disclosed methods of treating a non-immunogenic cancer in a subject and/or inducing PD-1/PD-L1 blockade inhibitor susceptibility in a tumor in a subject with a cancer can include any PD-1/PD-L1 blockade inhibitor known in the art, including, but not limited to nivolumab, pembrolizumab, pidilizumab, atezolizumab, avelumab, durvalumab, and BMS-936559). Thus, in one aspect, disclosed herein are methods of treating a non-immunogenic cancer in a subject and/or inducing blockade inhibitor susceptibility (such as, for example, PD-1/PD-L1, CTLA-4/B7-1/2, and/or CD47/SIRPα inhibitor susceptibility) in a tumor in a subject with a cancer comprising administering to the subject a hydrogel matrix comprising a chemotherapeutic agent and a blockade inhibitor; wherein the blockade inhibitor is a PD-1/PD-L1 blockade inhibitor such as, for example, nivolumab, pembrolizumab, pidilizumab, atezolizumab, avelumab, durvalumab, and/or BMS-936559; a CTLA-4/B7-1/2 inhibitor such as, for example, Ipilimumab; and/or a CD47/SIRPα inhibitor such as, for example Hu5F9-G4, CV1, B6H12, 2D3, CC-90002, and/or TTI-621. In one aspect, it is understood and herein contemplated that the hydrogel matrix for use in the disclosed methods can be configured to comprise 1, 2, 3, 4, 5, 6, 7, 8, 9, 10, 11, 12, 13, 14, or 15 blockade inhibitors simultaneously.

It is understood and herein contemplated that the hydrogel matrix can be designed to be bioresponsive to the microenvironment of the tumor and release the chemotherapeutic agent and/or blockade inhibitor (such as, for example, PD-1/PD-L1, CTLA-4/B7-1/2, and/or CD47/SIRPα blockade inhibitor) upon exposure to factors within the microenvironment such as, for example reactive oxygen species, including, but not limited to peroxides (for example hydrogen peroxide), superoxide, hydroxyl radical, and singlet oxygen the presence of acidity; redox potential (glutathione (GSH)); specific tumor-associated enzymes; hypoxia; and adenosine-5'-triphosphate (ATP).

In one aspect, it is contemplated herein that the hydrogel matrix used in the disclosed methods of treating/inhibiting/reducing a non-immunogenic cancer in a subject and/or inducing blockade inhibitor susceptibility (such as, for example, PD-1/PD-L1, CTLA-4/B7-1/2, and/or CD47/SIRPα inhibitor susceptibility) in a tumor in a subject with a cancer can release the chemotherapeutic and the blockade inhibitor (such as, for example, a PD-1/PD-L1, CTLA-4/B7-1/2, and/or CD47/SIRPα blockade inhibitor) are released from the hydrogel at the same rate or at different rates. The hydrogel can be designed to release the chemotherapeutic and PD-1/PD-L1 blockade inhibitor into the tumor microenvironment for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. Accordingly, in one aspect, disclosed herein are methods of treating a non-immunogenic cancer in a subject and/or inducing blockade inhibitor susceptibility (such as, for example, PD-1/PD-L1, CTLA-4/B7-1/2, and/or CD47/SIRPα inhibitor susceptibility) in a tumor in a subject with a cancer can release the chemotherapeutic and the blockade inhibitor(s) (such as, for example, PD-1/PD-L1, CTLA-4/B7-1/2, and/or CD47/SIRPα inhibitors) are released from the hydrogel for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

It is understood and herein contemplated that the disclosed methods of treating/inhibiting/reducing a non-immunogenic cancer in a subject and/or inducing blockade inhibitor susceptibility (such as, for example, PD-1/PD-L1, CTLA-4/B7-1/2, and/or CD47/SIRPα inhibitor susceptibility) in a tumor in a subject with a cancer can be used to treat any disease, disorder, or condition wherein uncontrolled cellular proliferation occurs such as cancers.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

A representative but non-limiting list of cancers that the disclosed compositions can be used to treat is the following: lymphoma; B cell lymphoma; T cell lymphoma; mycosis fungoides; Hodgkin's Disease; leukemias, including but not limited to myeloid leukemia; plasmacytomas; histiocytomas; bladder cancer; brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung; colon cancer; cervical cancer; cervical carcinoma; breast cancer; epithelial cancer; renal cancer, genitourinary cancer; pulmonary cancer; esophageal carcinoma; head and neck carcinoma; large bowel cancer; hematopoietic cancers; testicular cancer; colon and rectal cancers; prostatic cancer; AIDS-related lymphomas or sarcomas, metastatic cancers, or cancers in general; or pancreatic cancer.

Thus, in one aspect, disclosed herein are methods of treating a cancer and/or inducing PD-1/PD-L1 blockade inhibitor susceptibility in a tumor in a subject with a cancer, wherein the cancer a cancer with low PD-L1 expression or a non-immunogenic cancer selected from the group consisting of melanoma, non-small cell lung carcinoma, renal cancer, head and neck cancer, and/or bladder cancer.

C. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 2:
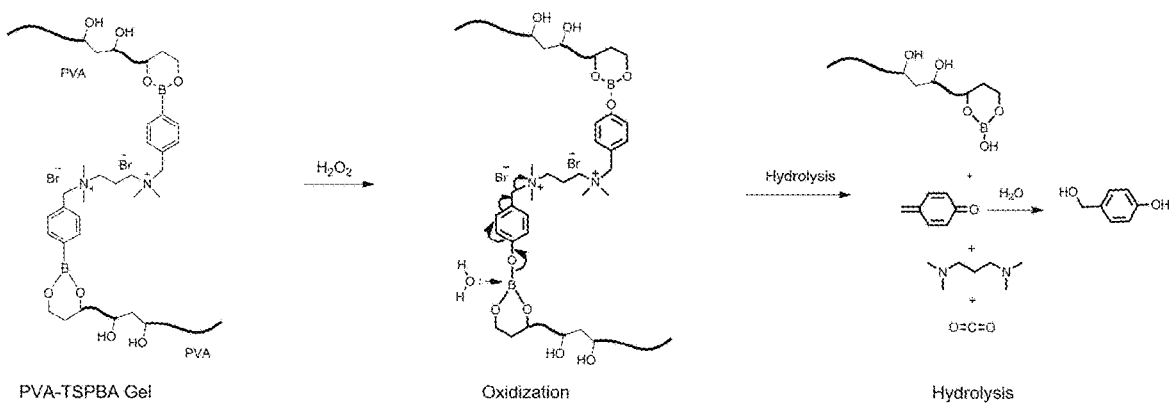
FIG. 2 shows a schematic of the $H_2O_2$-responsiveness mechanism of PVA-TSPBA gels.
Figures 3A, 3B:
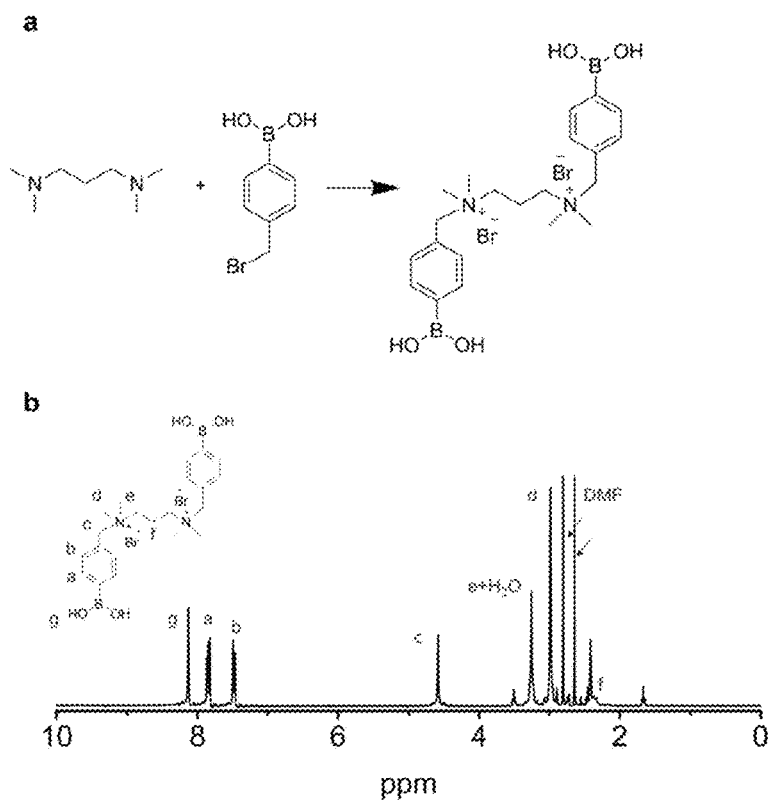
FIG. 3A shows the synthesis route of TSPBA.
FIG. 3B shows 1H-NMR (300 MHz, in d-DMSO) spectrum of TSPBA based on at least triplicate measurements.

1. Example 1: In Situ Formed Reactive Oxygen Species-Responsive Scaffold with Gemcitabine and Checkpoint Inhibitions for Synergistic Immunotherapy a) Results ROS-responsive hydrogel was obtained by crosslinking poly (vinyl alcohol) (PVA) with a ROS-labile linker: $N^1$-(4-boronobenzyl)-$N^3$-(4-boronophenyl)-$N^1,N^1,N^3,N^3$-tetramethylpropane-1,3-diaminium (TSPBA) (FIG. 2), which was synthesized via quaternization reaction of $N^1,N^1,N^3,N^3$-tetramethylpropane-1,3-diamine with an excess of 4-(bromomethyl) phenylboronic acid (FIG. 3). TSPBA contains two phenylboronic acids that complex with multiple diols on PVA. Formation of PVA-TSPBA hydrogel was further confirmed by a rheology test. Addition of TSPBA to PVA solution led to rapid increase in the elastic modulus (G'), demonstrating the formation of a network between the PVA chains. The hydrogel can be quickly formed after mixing the PVA and linkers through a dual syringe (FIG. 1a). In vivo gel formation and degradation were examined in healthy mice. The integrity of the gels remained up to 7 days, while the overall size of gels decreased gradually. At week 3 following injection, the gels were no longer found at the injection sites, indicating their biodegradability.

GEM and aPD-L1 at therapeutic relevant doses were encapsulated into the PVA-TSPBA hydrogel. The drug-loaded hydrogels showed similar rheology properties compared with the blank one, indicating that the formation of the hydrogel was not affected by the drug encapsulation. The morphology of the dried scaffold network was clearly observed by the cryo-scanning electron microscopy (Cryo-SEM), with a swollen pore size of about 0.5 μm (FIG. 1b). To visualize the distribution of therapeutics in the hydrogels, fluorescein (FITC) as fluorescent surrogate for GEM and Cy5.5-labeled aPD-L1 were loaded into the hydrogel. From the confocal image of a frozen section of hydrogel, FITC displayed a uniform distribution, while the dotted signals associated with aPD-L1 were detected inside the hydrogel (FIG. 1c).

The TSPBA can be oxidized and hydrolyzed when exposed to $H_2O_2$ in the TME, leading to the dissociation of the polymeric scaffold and the release of PVA and payloads. To verify the ROS-sensitive degradability of the hydrogels, samples were immersed in phosphate-buffered saline (PBS) containing 0.1 mM $H_2O_2$ at 37° C. Changes in the morphology of the scaffolds were clearly observed over time (FIG. 1d). The release profiles of GEM and aPD-L1 were quantified using high-performance liquid chromatography (HPLC) and enzyme-linked immunosorbent assay (ELISA), respectively. As expected, GEM and aPD-L1 were released form the hydrogel in $H_2O_2$ solution in a triggered manner compared to that of the control PBS. The great majority of GEM was released within one day, whereas aPD-L1 showed a more sustained release profile with 80% release within three days (FIG. 1e-f). The release pattern was further examined in vivo after the intratumor injection of the drug-loaded scaffolds in the B16F10 mouse model. Confocal imaging of tumor sections (FIG. 4) showed that the FITC signal (fluorescent surrogate for GEM) was rapidly evident (within day 1), while the signal corresponding to aPDL1 increased gradually within 3 days, which is consistent with the in vitro study. These distinct release dynamics facilitated the delivery of GEM and aPD-L1 into the TME for the intended sequential effects.

Next, the response of immune cells and tumor cells was measured after GEM@Gel treatment in vivo. GEM was loaded into the hydrogel and injected peritumorally. It was found that a high-dose of GEM (25 mg/kg) within the GEM@Gel significantly depleted the TIL (FIG. 5a), and had no significant effects on the tumor free survival (FIG. 5b-c). In contrast, blank hydrogel or low-dose of GEM (5 mg/kg) within the GEM@Gel increased the absolute number of TIL at the tumor site (FIG. 6a-b). To further assess the overall immune effects of low dose of GEM@Gel within the TME, the intratumoral presence of ROS, regulatory T cells (Tregs), myeloid-derived suppressor cells (MDSCs) and tumor-associated macrophages (TAMs) was examined. Intratumoral ROS levels were significantly reduced after the blank hydrogel or GEM@Gel implantation. Furthermore, while Tregs were not significantly affected, a significant reduction of MDSCs (CD45+CD11b+Gr-1+) and M2-polarized TAMs (CD206hiCD11b+F4/80+) (FIG. 6c-d) was observed. Interestingly, significant reduction of TAMs (percentage of CD206hiCD11b+F4/80+ within total cells) was also observed in mice treated with blank hydrogel (FIG. 6d). Taken together, these data indicate that GEM@Gel enhances the frequency of TIL and reduce other immunosuppressive cellular components.

Treatment of B16F10 cancer cells in vitro with GEM resulted in cell death and increased expression of PD-L1 in surviving cells. PD-L1 expression on B16F10 cancer cells was found GEM-dose- and time-dependent as assessed by flow cytometry, immunofluorescence and western blot (FIG. 7a-b). In in vivo study, GEM@Gel also induced PD-1 expression in both CD4+ and CD8+ TIL, as well as PD-L1 expression on cancer cells, dendritic cells and macrophages compared to the untreated tumors and tumors treated with blank hydrogels (FIG. 6e-f). PD-L1 expression in the tumor cells was also displayed in a time dependent fashion showing a significant increase in mean fluorescence intensity by 24 hours following treatment and even greater increase 48 hours post treatment. Circulating type 1 T helper (Th1) cytokines were also measured before and after GEM@Gel implantation (FIG. 6g). Among them, IL-6 and IFN-γ were found significantly upregulated after GEM@Gel implantation (FIG. 6g), and IFN-γ is known to induce PD-L1 expression in tumor cells. These data substantiated that GEM@Gel can elicit an inflamed and immunogenic TME.

To validate if the proposed synergistic chemo-immunotherapy strategy can promote antitumor effects, the B16F10 mouse melanoma tumor model was utilized. Tumor-bearing mice were implanted peritumorally with GEM@Gel (200 µL, 10% w/w) (GEM: 5 mg/kg), aPD-L1@Gel (aPDL1: 50 µg per mouse) or GEM-aPD-L1@Gel (aPD-L1: 50 µg per mouse, GEM: 5 mg/kg). Tumor growth was monitored by the bioluminescence signals of B16F10 cells (FIG. 8a). The blank hydrogel and GEM@Gel showed similar effects and were not superior to untreated control. aPD-L1@Gel treated mice showed a delay of tumor growth. In contrast, 6 of 10 mice receiving GEM-aPD-L1@Gel showed no detectable tumor (FIG. 8b-c). The tumor sizes in mice also correlated with their survival. Sixty percent of mice survived at least 60 days after treatment with GEM-aPD-L1@Gel with undetectable tumors. In contrast, none of the mice survived in all control groups after two months (FIG. 3d). GEM-aPD-L1@Gel was compared with non-encapsulated GEM and aPD-L1. GEM-aPD-L1@Gel treatment was superior in inhibiting tumor growth compared non-encapsulated drugs delivered locally or systemically (FIG. 9).

Furthermore, tumors were harvested and analyzed by immunofluorescence and flow cytometry on day 10 after treatments. GEM-aPD-L1@Gel-treated mice showed remarkable infiltration with CD8+ and CD4+ T cells compared with control mice (FIG. 8e). Tumor weights were also significantly lower in the GEM-aPD-L1@Gel-treated mice on day 10, which paralleled an increase in absolute numbers of TIL. More strikingly, the absolute number of CD8+ T cells/gram of tumor increased by more than 20-fold in the GEM-aPD-L1@Gel treated mice compared with the untreated control and 2.5-fold over the aPD-L1@Gel treated mice (FIG. 8f). Additionally, the intratumoral ratios of T effector cells to Tregs were significantly increased in mice after GEM-aPD-L1@Gel therapy (FIG. 8g-i). Taken together, these observations indicate that GEM-aPD-L1@Gel implantation triggers a robust T cell-mediated anti-tumor immune response.

Figure 11:
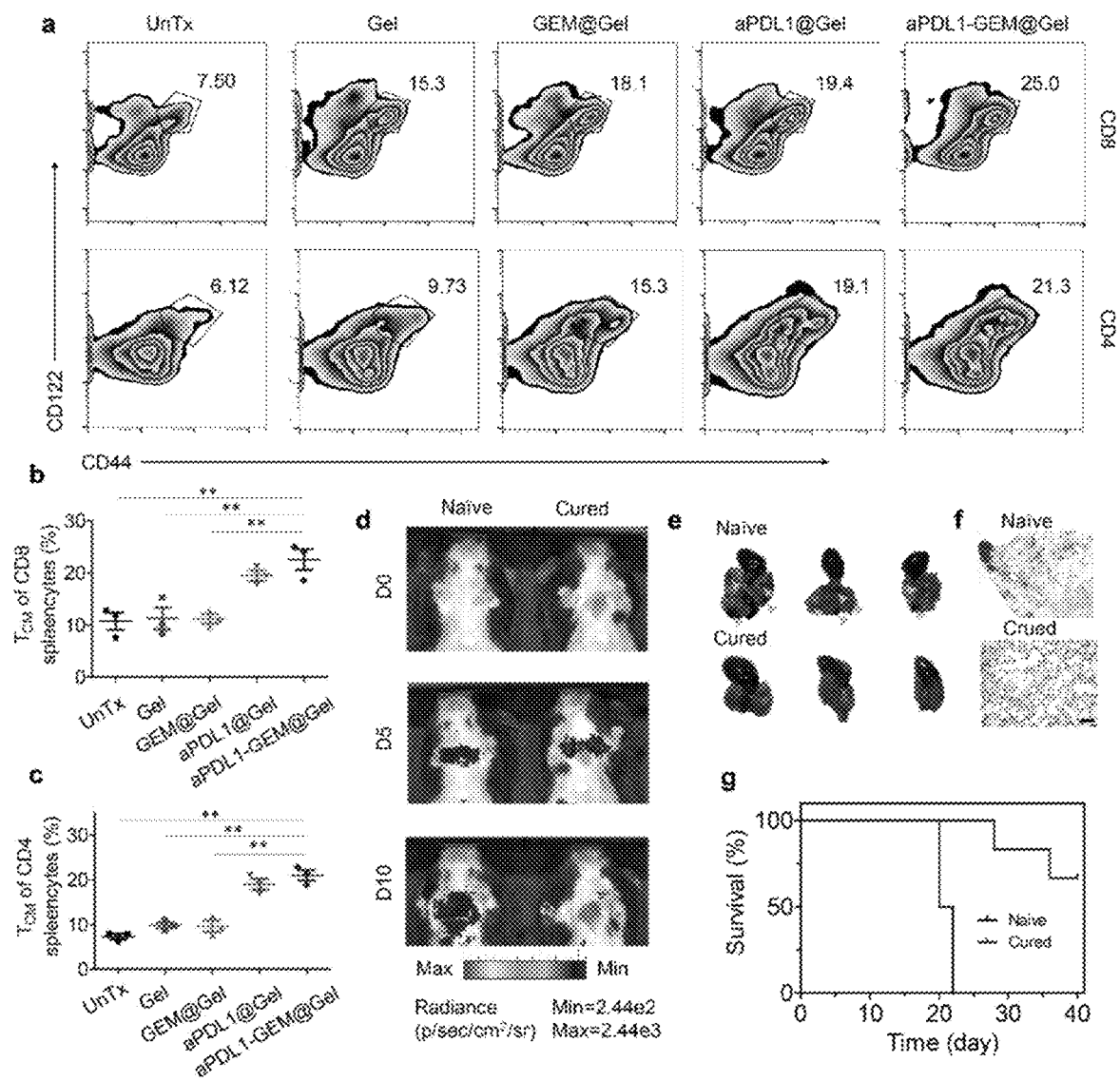

To assess whether the local delivery of GEM-aPD-L1@Gel also induces systemic immune responses, tumor cells were inoculated on the opposite site of the primary tumor in which the hydrogel was implanted (FIG. 10a). It was observed that PD-L1 was upregulated by tumor cells at both tumor sites compared to tumors in the untreated mice (FIG. 10b-c). This can be explained by the systemic distribution of IFN-γ locally induced by GEM-aPD-L1@Gel implant (FIG. 6g). Blocking systemic IFN-γ by a neutralizing antibody can significantly affect the PD-L1 upregulation in the distant tumor. Furthermore, tumor bioluminescence (FIG. 10d-e) and tumor weight (FIG. 10f) significantly decreased in both hydrogel-implanted and untreated tumor sites (FIG. 10g) with corresponding equal infiltration of CD3+CD8+ T cells compared with the untreated control mice (FIG. 10h-i). T cell-memory response was also generated in mice treated with GEM-aPD-L1@Gel, as they showed significantly increased frequency of endogenous CD44+CD122hi central memory T cells (TCM) in the spleen as compared to the control groups (FIG. 11a-c). When re-challenged with tumor cells, mice that had no detectable tumors after treatment with GEM-aPD-L1@Gel did not show significantly tumor growth as clearly indicated by bioluminescence imaging of lung (FIG. 11d) and H&E staining (FIG. 11e-f). Overall survival was also found to be significantly better compared with control group (FIG. 11g). These collective results indicate that systemic antitumor effects and memory T cell formation can be achieved by local delivery of GEM-aPD-L1@Gel.

To further demonstrate that the proposed chemo-immunotherapy is broadly applicable, the 4T1 tumor model of triple-negative breast cancer (TNBC) was implemented. 4T1 cells were reported to express low levels of PD-L1. In vitro experiments showed that GEM induced PD-L1 expression in 4T1 cancer cells (FIG. 12). For in vivo study, 4T1 were inoculated subcutaneously into the right flank of female BABL/c mice. After 7 days, the mice bearing 4T1 tumors were treated with GEM@Gel (200 µL, 10% w/w) (GEM: 5 mg/kg), aPD-L1@Gel (aPDL1: 50 µg per mouse) or GEM-aPD-L1@Gel (aPD-L1: 50 µg per mouse, GEM: 5 mg/kg). Encouragingly, it was also found that GEM-aPD-L1@Gel promoted anticancer effects in 4T1-bearing mice as indicated by the bioluminescence imaging (FIG. 13a). Tumor growth was also significantly suppressed in mice treated with GEM-aPD-L1@Gel (FIG. 13b), which also prolonged survival rate (FIG. 13c).

Toxic effects always need serious concern when studying combination therapies. In the study, the hydrogels were completely degraded 40 days after implantation without inflammatory response, indicating their excellent biodegradability and biocompatibility. PVA with higher molecular weight is considered to be highly compatible and eliminated from the body via biliary excretion. Body weights of mice were not significantly affected after receiving hydrogels loaded with GEM and aPD-L1. In addition, histology analysis of organs obtained from mice 40 days after treatment indicated no appreciable abnormality or noticeable organ damage.

To further investigate the potency of the in situ-formed ROS-responsive scaffold, experiments in a B16F10 incomplete-tumor-resection model were performed. ROS-response scaffolds containing GEM, aPD-L1 or both were directly injected into the resection cavity. Systemically or locally administered non-encapsulated drugs were also included as control groups. Mice receiving GEM-aPD-L1@Gel were more protected from local tumor recurrence (30% tumor recurrence rate) (FIG. 14a-d), with significantly higher survival rate compared to other groups (FIG. 14e). No obvious systemic toxicities were observed in vivo according to the body weight. In addition, similar results were obtained in the 4T1 tumor recurrence model (as luciferase itself is quite immunogenic, non-luc-expressing 4T1 tumor was used here to avoid any immune response against the luciferase reporter) (FIG. 15). GEM-aPD-L1@Gel treatment prevented cancer recurrence without obvious toxicity (FIG. 15). Meanwhile, although the 4T1 breast cancer model has high metastatic potential, metastatic lesions were not found in the lungs as compared to other groups. Collectively, these results indicate that ROS-response scaffolds serve as an effective depot to enhance ICB after surgery to prevent cancer recurrence.

b) Discussion

It is demonstrated herein that an in situ-formed hydrogel scaffold consisting of a ROS-sensitive moiety can deliver locally GEM and aPD-L1 with distinct kinetics in tumor bearing mice to promote an immunogenic tumor phenotype and immune-mediated tumor rejection.

PD-L1 expression in tumor cells and TIL is considerably elevated after chemotherapy, resulting in PD-L1-mediated T cell exhaustion. Herein it was determined that synergistic anticancer efficacy can be achieved by distinct kinetics and local administration of chemotherapy and ICB. To achieve this cascade treatment at the tumor site, a ROS-responsive hydrogel scaffold was synthesized and loaded with GEM and aPD-L1, taking into account that ROS is particularly abundant in the TME. After in situ construction, the ROS-responsive hydrogel released both GEM and aPD-L1 in a ROS-dependent manner. Of note, the smaller molecular weight of GEM compared to aPD-L1 contributed to its faster release from the hydrogel.

GEM is a ribonucleotide reductase inhibitor that has a broad spectrum of antitumor activity. Significant upregulation of PD-L1 and PD-1 expression was observed in tumor cells and TIL, respectively upon exposure to low-dose GEM@Gel. Remarkably, GEM@Gel also caused a significant reduction of tumor-infiltrating MDSCs that contributed in causing dysfunction of effector T cells. Since GEM is known to inhibit intratumoral MDSCs, their depletion upon the implantation of GEM@Gel was not surprising. Following a similar pattern, GEM@Gel also induced an enhancement of T cell infiltration and a significant loss of TAMs expressing CD206. However, loss of TAMs and reduction of ROS were also observed in mice treated with the blank hydrogel. Since ROS is critical for the macrophage differentiation, ROS depletion caused by the hydrogel can contribute in recruiting T cells into the tumor site as well as blocking M2-macrophage differentiation. Therefore, the ROS-responsive scaffold not only acts as a reservoir to control the release of therapeutics, but also plays as a scavenger of ROS within the TME to achieve synergistic treatment efficacy.

GEM-aPD-L1@Gel induced an immunogenic tumor phenotypes and the following activity of the aPD-L1 promotes tumor regression in the B16F10 melanoma and 4T1 breast tumor (relative low-PD-L1 expression)-bearing mouse models. Moreover, the local treatment generated a systematic anticancer immune response that prevented distant tumor growth. Collectively, the proposed synergistic chemo-immunotherapy strategy offers new opportunities in treating low-immunogenic tumors whilst preventing systemic toxicities. Furthermore, the scaffold can also be applied to the surgical bed of resected tumors, which is also particularly abundant in ROS, making this strategy clinically relevant for preventing cancer recurrence postoperatively. Of note, although resection of tumour is thought to remove the disable tumour driven immunosuppression, there are studies indicating that inflammation induced by surgical approaches can also promote the risk of tumor recurrence. The scaffold generated inside the resection cavity can contribute to scavenging ROS and thus reduce the inflammation. Finally, although ICB is considered tolerated by the patients, combination therapy can increase the risk of the side effects. In this study, it was found that one mouse treated with systemic administration of free drugs showed about 10% loss of body weight, while no toxicity was observed in mice treated with the drug-loaded scaffolds.

In summary, a synergistic chemoimmunotherapy strategy was developed based on control release of chemotherapeutic drug and ICB from a TME-responsive hydrogel scaffold. Low-dose GEM released by the hydrogel scaffold elicits immunogenic phenotypes of tumors by upregulating of PD-L1 and PD-1 on tumor cells and TIL, respectively, and by depleting TAMs and MDSCs within the tumor. Importantly, the ROS-responsive gels can not only serve as a reservoir for tuned release of therapeutics, but also play as a scavenger of ROS and thus further enhance the immunogenic phenotypes. This strategy holds promise in treating low-immunogenic tumors currently non responsive to ICB. Moreover, since local implantation of the scaffolds promotes systemic immune responses and T cell memory formation, this strategy can be used to treat metastatic tumors and prevent tumor recurrence.

c) Materials and Methods (1) Study Design

The objective of the study was to develop a strategy based on control release of chemotherapeutic drug and ICB from a TME-responsive hydrogel scaffold for enhancing response and efficiency of ICB therapy. The in vivo antitumor efficacy was assessed in B16F10 or 4T1 tumor and incomplete-tumor-resection models. Mice from varying treatment groups were followed to create survival curves, imaged to assess tumor progression, and rechallenged with tumor to assess immune memory. Sample size (n=5-10 per group) was determined based on experience. Animals were randomly assigned to groups on the basis of tumor size and body weight. The investigators were not blinded to allocation during experiments and outcome assessment. Animals were euthanized when exhibiting signs of impaired health or when the volume of the tumour exceeded 1.5 cm 3. All experiments were run at least in triplicates.

(2) Materials.

All chemicals were purchased from Sigma-Aldrich unless otherwise specified and were used as received. Gemcitabine hydrochloride (United States Pharmacopeia (USP) reference standard) was purchased from Sigma (Cat. #: 1288463), Anti-PDL1 antibody (aPDL1) used in vivo was purchased from Biolegend Inc (Cat. #124329, Clone: 10F.9G2).

(3) Synthesis of TSPBA.

N,N,N',N'-tetramethyl-1,3-propanediamine (0.1 g, 1.5 mmol) and 4-(bromomethyl) phenylboronic acid (0.5 g, 4.6 mmol) were dissolved in dimethylformamide (DMF) (10 mL) respectively and mixed together. After stirring at 60° C. overnight, the mixture was poured into THF (100 mL), filtrated, and washed by THF (3×20 mL). After dried under vacuum overnight, pure TSPBA (0.3 g, yield 70%) was obtained. 1H-NMR (300 MHz, d-DMSO, δ): 8.132 (s, 4H), 7.85 (d, 4H), 7.49 (d, 4H), 4.58 (s, 4H), 3.26 (s, 4H), 2.97 (s, 12H), 2.38 (m, 2H) (FIG. 3).

(4) Formation of PVA-TSPBA Hydrogels.

PVA (Mw=72 KDa, 98% hydrolyzed, 5 g) and DI water (100 mL) were mixed together and stirred at 90° C. to acquire a clear solution. TSPBA (5 wt % in $H_2O$, 2 mL) and PVA (5 wt % in $H_2O$, 2 mL) were mixed together and a hydrogel was formed instantly, which was used for in vitro experiments. For the fabrication of GEM and aPDL1 loaded gel, predetermined amount of GEM or aPDL1 were added to PVA aqueous solution. For in vivo application, PVA and TSPBA aqueous solution were loaded into a dual syringe and injected directly to tumors to form a gel in situ.

(5) Characterization of aPDL1-GEM@Hygrogels.

Cryo-SEM imaging was obtained by JEOL 7600F with Gatan Alto. Fluorescence imaging was analyzed using a confocal microscope (Zeiss LSM 710). Dynamic rheological behavior of PVA before and after gelation at 25° C. was measured using a TA Instruments AR-2000 stress controlled rheometer with 25 mm aluminum cross-hatched parallel plates.

(6) GEM and aPDL1 Release from PVA-TSPBA Hydrogels.

Release studies were performed at 37° C. with constant agitation in PBS. $H_2O_2$ (1 mM) (Sigma) were added to samples to study the GEM and antibody release. The released GEM was analyzed by HPLC and the antibody release was determined by Rat IgG total ELISA kit (eBioscience).

(7) In Vivo Tumor Models.

To test the anticancer effects on mice model, 9 or 14 days after $1\times10^6$ either luciferase-tagged B16F10 or 4T1 tumor cells were transplanted into the right flank of mice (the tumor reaches ~100 mm³). Mice were weighed and randomly divided into different groups (n=7-10). The mice were locally implanted with different formulations peritumorally, including hydrogels, GEM@Ggel, aPDL1@Gel and aPDL1-GEM@Gel (aPDL1: 50 µg per mouse, GEM: 5 mg/kg, 200 µL, 10% w/w). The tumor burden was monitored by the bioluminescence signal of cancer cells. Images were taken using an IVIS Lumina imaging system (Caliper, USA). The tumors were also measured with a digital caliper. The tumor volume (mm³) was calculated as (long diameter× short diameter 2)/2.

To measure the effects on cancer recurrence, 9 or 14 days after 1×10 6 either B16F10 (or 4T1) or luciferase-tagged B16F10 (or 4T1) tumor cells were transplanted into the right flank of mice, the tumors (the size reaches ~100 mm³) were resected leaving about 1% residual tissue behind to mimic the residual microtumors in surgical bed. Briefly, animals were anesthetized with isoflurane (1-3% for maintenance; up to 5% for induction) anesthesia via chamber induction and maintained via nose cone. The amount of residual tumor tissue was determined by the bioluminescence signals of tumor cells before and after resection. The tumor area was clipped and aseptically prepped. Sterile instruments were used to remove roughly 99% of the tumor. The amount of residual tumor tissue was determined by the integrated bioluminescence signal intensity of the tumor tissues before and after tumor resection. The wound was closed by Autoclip wound clip system. Mice were weighed and randomly divided into different groups (n=7-10). After surgery, the mice were implanted with different formulations into surgical bed, including hydrogels, GEM@Gel, aPDL1@Gel and aPDL1-GEM@Gel. Free GEM+aPDL1 with same dose was locally or systematically administered into mice after resection of primary tumor. The tumor burden was monitored by the bioluminescence signal of cancer cells. The mice were clipped and shaved using a depilatory cream before imaging if necessary. The tumors were also measured with a digital caliper. The tumor volume (mm³) was calculated as (long diameter×short diameter 2)/2. Animals were euthanized with carbon dioxide when exhibiting signs of impaired health or when the volume of the tumor exceeded 1.5 cm³.

(8) In Vivo Bioluminescence and Imaging.

Bioluminescence images were collected with an IVIS Spectrum Imaging System (Perkin Elmer Ltd). Living Image software (Perkin Elmer Ltd) was used to acquire the data 10 min after intraperitoneal injection of d-luciferin (Thermo Scientific™ Pierce™) in DPBS (15 mg/mL) into the animals (10 µL/g of body weight). Exposure time for bioluminescence imaging was 5 min. Regions of interest (ROI) were quantified as average radiance (photons $s^{-1}$ $cm^{-2}$ $sr^{-1}$, represented by color bars) (IVIS Living Image 4.2).

(9) Cell Lines.

The mouse melanoma cell line B16F10 and mouse mammary carcinoma cell line 4T1 were purchased from the American Type Culture Collection. B16F10-luc-GFP and 4T1-luc-GFP cells were gifts from Dr. Leaf Huang at the University of North Carolina at Chapel Hill. B16F10 cells were maintained in Dulbecco's Modified Eagle Medium (Gibco, Invitrogen) supplemented with 10% fetal bovine serum (Invitrogen, Carlsbad, CA), 100 U/mL penicillin (Invitrogen), and 100 U/mL streptomycin (Invitrogen). 4T1 cells were maintained in RPMI-1640 Medium (Gibco, Invitrogen) supplemented with 10% fetal bovine serum (Invitrogen, Carlsbad, CA), 100 U/mL penicillin (Invitrogen), and 100 U/mL streptomycin (Invitrogen). Master and working cell banks were generated immediately upon receipt. The third and fourth passages were used for the experiments. Cells were tested every three months to exclude the presence of mycoplasma. Authentication of cells was not performed after receipt.

(10) Mice.

C57BL/6 mice and BALB/c mice were purchased from Jackson Lab (USA). Age-matched (6-10 weeks) female were used throughout all experiments. We performed all mouse studies in accordance with the animal protocol approved by the Institutional Animal Care and Use Committee at the University of North Carolina at Chapel Hill and North Carolina State University. Experimental group sizes were approved by the regulatory authorities for animal welfare after being defined to balance statistical power, feasibility, and ethical aspects. All mice were kept in accordance with federal and state policies on animal research at the University of North Carolina at Chapel Hill and North Carolina State University.

(11) Antibodies.

Anti-PDL1 antibody (aPDL1) used in vivo was purchased from Biolegend Inc (Cat. #124329, Clone: 10F.9G2). Antibodies used for flow cytometry included CD3 (Thermo Fisher Scientific, Cat. #A18644), CD4 (Thermo Fisher Scientific, Cat. #A18667), CD8 (Thermo Fisher Scientific, Cat. #A18609), PD1 (Biolegend, Cat. #135227), CD11c (Biolegend, Cat. #117309), PDL1 (Biolegend, Cat. #124311), CD11b (Biolegend, Cat. #101211), and intracellular Foxp3 (eBioscience, Cat. #71-5775-40). The stained cells were analyzed on a Calibur FACS instrument (BD). A minimum of 1000 events per plot were collected and analyzed using FlowJo software (version 10). Secondary antibodies including goat anti-rat IgG (H+L) (Thermo Fisher Scientific, Cat. #A18866), rabbit anti-rat IgG (H+L) (Thermo Fisher Scientific, Cat. #A18920) and goat anti-rat IgG (minimal x-reactivity) (Biolegend, Cat. #405408) were used for immunostaining.

(12) Cytokine Detection.

The plasma levels of IL-2, IL-6, IL-10, IFN-γ and TNF-α were measured by LEGENDplex™ Mouse Th1 Panel multiple assay (Biolegend, Cat. #740025) according to the manufacturer's instructions. The plasma was collected from mice before and two days after GEM@Gel implantation.

(13) Confocal Microscopy.

Harvested tumors were dissected and snap frozen in O.C.T. Micrometer sections were cut using a cryotome and mounted on slides. Sections were fixed in ice-cold acetone for 10 minutes prior to rehydration with PBS. After blocking with BSA (3%), sections were stained with primary antibodies overnight at 4° C. Following the addition of fluorescence-labeled secondary antibodies, the slides were analyzed using a confocal microscope (Zeiss LSM 710).

(14) Statistical Analysis.

All results are expressed as mean±s.d., mean±s.e.m. as indicated. Biological replicates were used in all experiments unless stated otherwise. One-way analysis of variance (ANOVA) was performed when more than two groups were compared, and when determined significant (P<0.05), multiple comparisons were performed using Tukey's post-hoc test. Survival was determined with the log-rank test. All statistical analyses were performed with GraphPad Prism (5.0). *P<0.05, P<0.01, *P<0.005.

D. References

A. J. Vegas, O. Veiseh, J. C. Doloff, M. Ma, H. H. Tam, K. Bratlie, J. Li, A. R. Bader, E. Langan, K. Olejnik, Combinatorial hydrogel library enables identification of materials that mitigate the foreign body response in primates. *Nat. Biotechnol.* 34, 345-352 (2016).

A. M. Cook, W. J. Lesterhuis, A. K. Nowak, R. A. Lake, Chemotherapy and immunotherapy: mapping the road ahead. *Curr. Opin. Immunol.* 39, 23-29 (2016).

A. M. Rosales, K. S. Anseth, The design of reversible hydrogels to capture extracellular matrix dynamics. *Nat. Rev. Mater.* 1, 15012 (2016).

B. A. Pulaski, S. Ostrand-Rosenberg, Mouse 4T1 breast tumor model. *Curr. Protoc. Immunol.*, 20.22. 21-20.22. 16 (2001).

C. Boutros, A. Tarhini, E. Routier, O. Lambotte, F. L. Ladurie, F. Carbonnel, H. Izzeddine, A. Marabelle, S. Champiat, A. Berdelou, E. Lanny, M. Texier, C. Libenciuc, A. M. Eggermont, J. C. Soria, C. Mateus, C. Robert, Safety profiles of anti-CTLA-4 and anti-PD-1 antibodies alone and in combination. *Nat. Rev. Clin. Oncol.* 13, 473-486 (2016).

C. Dunnill, T. Patton, J. Brennan, J. Barrett, M. Dryden, J. Cooke, D. Leaper, N. T. Georgopoulos, Reactive oxygen species (ROS) and wound healing: the functional role of ROS and emerging ROS-modulating technologies for augmentation of the healing process. *Int. Wound J.* 14, 89-96 (2017).

C. Nathan, A. Cunningham-Bussel, Beyond oxidative stress: an immunologist's guide to reactive oxygen species. *Nat. Rev. Immunol.* 13, 349-361 (2013).

C. Pfirschke, C. Engblom, S. Rickelt, V. Cortez-Retamozo, C. Garris, F. Pucci, T. Yamazaki, V. Poirier-Colame, A. Newton, Y. Redouane, Y. J. Lin, G. Wojtkiewicz, Y. Iwamoto, M. Mino-Kenudson, T. G. Huynh, R. O. Hynes, G. J. Freeman, G. Kroemer, L. Zitvogel, R. Weissleder, M. J. Pittet, Immunogenic Chemotherapy Sensitizes Tumors to Checkpoint Blockade Therapy. *Immunity* 44, 343-354 (2016).

C. Wang, W. Sun, Y. Ye, Q. Hu, H. N. Bomba, Z. Gu, In situ activation of platelets with checkpoint inhibitors for post-surgical cancer immunotherapy. *Nat. Biomed. Eng.* 1, 0011 (2017).

C. Wang, Y. Ye, G. M. Hochu, H. Sadeghifar, Z. Gu, Enhanced Cancer Immunotherapy by Microneedle Patch-Assisted Delivery of Anti-PD1 Antibody. *Nano Lett.* 16, 2334-2340 (2016).

C. Wang, Y. Ye, Q. Hu, A. Bellotti, Z. Gu, Tailoring Biomaterials for Cancer Immunotherapy: Emerging Trends and Future Outlook. *Adv. Mater*, (2017).

D. B. Johnson, J. M. Balko, M. L. Compton, S. Chalkias, J. Gorham, Y. Xu, M. Hicks, I. Puzanov, M. R. Alexander, T. L. Bloomer, J. R. Becker, D. A. Slosky, E. J. Phillips, M. A. Pilkinton, L. Craig-Owens, N. Kola, G. Plautz, D. S. Reshef, J. S. Deutsch, R. P. Deering, B. A. Olenchock, A. H. Lichtman, D. M. Roden, C. E. Seidman, I. J. Koralnik, J. G. Seidman, R. D. Hoffman, J. M. Taube, L. A. Diaz, Jr., R. A. Anders, J. A. Sosman, J. J. Moslehi, Fulminant Myocarditis with Combination Immune Checkpoint Blockade. *N. Engl. J. Med.* 375, 1749-1755 (2016).

D. I. Gabrilovich, S. Nagaraj, Myeloid-derived suppressor cells as regulators of the immune system. *Nat. Rev. Immunol.* 9, 162-174 (2009).

D. Killock, Lung cancer: Anti-PD-1 therapy in the frontline. *Nat. Rev. Clin. Oncol.* 13, 715 (2016).

D. Mathios, J. E. Kim, A. Mangraviti, J. Phallen, C.-K. Park, C. M. Jackson, T. Garzon-Muvdi, E. Kim, D. Theodros, M. Polanczyk, Anti-PD-1 antitumor immunity is enhanced by local and abrogated by systemic chemotherapy in GBM. *Sci. Transl. Med.* 8, 370ra180-370ra180 (2016).

D. R. Littman, Releasing the Brakes on Cancer Immunotherapy. *Cell* 162, 1186-1190 (2015).

E. Eriksson, J. Wenthe, S. Irenaeus, A. Loskog, G. Ullenhag, Gemcitabine reduces MDSCs, tregs and TGFβ-1 while restoring the teff/treg ratio in patients with pancreatic cancer. *J. Transl. Med.* 14, 282 (2016).

E. I. Buchbinder, F. S. Hodi, Melanoma in 2015: Immune-checkpoint blockade—durable cancer control. *Nat. Rev. Clin. Oncol.* 13, 77-78 (2016).

E. Nolan, P. Savas, A. N. Policheni, P. K. Darcy, F. Vaillant, C. P. Mintoff, S. Dushyanthen, M. Mansour, J.-M. B. Pang, S. B. Fox, Combined immune checkpoint blockade as a therapeutic strategy for BRCA1-mutated breast cancer. *Sci. Transl. Med.* 9, eaal4922 (2017).

E. Vacchelli, Y. Ma, E. E. Baracco, A. Sistigu, D. P. Enot, F. Pietrocola, H. Yang, S. Adjemian, K. Chaba, M. Semeraro, M. Signore, A. De Ninno, V. Lucarini, F.

Peschiaroli, L. Businaro, A. Gerardino, G. Manic, T. Ulas, P. Gunther, J. L. Schultze, O. Kepp, G. Stoll, C. Lefebvre, C. Mulot, F. Castoldi, S. Rusakiewicz, S. Ladoire, L. Apetoh, J. M. Bravo-San Pedro, M. Lucattelli, C. Delarasse, V. Boige, M. Ducreux, S. Delaloge, C. Borg, F. Andre, G. Schiavoni, I. Vitale, P. Laurent-Puig, F. Maffei, L. Zitvogel, G. Kroemer, Chemotherapy-induced antitumor immunity requires formyl peptide receptor 1. *Science* 350, 972-978 (2015).

G. T. Gibney, L. M. Weiner, M. B. Atkins, Predictive biomarkers for checkpoint inhibitor-based immunotherapy. *Lancet Oncol.* 17, e542-e551 (2016).

G. Y Liou, P. Storz, Reactive oxygen species in cancer. *Free Radic. Res.* 44, 479-496 (2010).

H. Tang, Y Wang, L. K. Chlewicki, Y Zhang, J. Guo, W. Liang, J. Wang, X. Wang, Y. X. Fu, Facilitating T Cell Infiltration in Tumor Microenvironment Overcomes Resistance to PD-L1 Blockade. *Cancer Cell* 30, 500 (2016).

I. Sagiv-Barfi, H. E. K. Kohrt, D. K. Czerwinski, P. P. Ng, B. Y Chang, R. Levy, Therapeutic antitumor immunity by checkpoint blockade is enhanced by ibrutinib, an inhibitor of both BTK and ITK. *Proc. Natl. Acad. Sci. U.S.A.* 112, E966-E972 (2015).

I. Segatto, S. Berton, M. Sonego, S. Massarut, T. Perin, E. Piccoli, A. Colombatti, A. Vecchione, G. Baldassarre, B. Belletti, Surgery-induced wound response promotes stem-like and tumor-initiating features of breast cancer cells, via STAT3 signaling. *Oncotarget* 5, 6267-6279 (2014).

J. A. Olson, C. McDonald-Hyman, S. C. Jameson, S. E. Hamilton, Effector-like CD8+ T cells in the memory population mediate potent protective immunity. *Immunity* 38, 1250-1260 (2013).

J. E. Rosenberg, J. Hoffman-Censits, T. Powles, M. S. van der Heij den, A. V. Balar, A. Necchi, N. Dawson, P. H. O'Donnell, A. Balmanoukian, Y Loriot, S. Srinivas, M. M. Retz, P. Grivas, R. W. Joseph, M. D. Galsky, M. T. Fleming, D. P. Petrylak, J. L. Perez-Gracia, H. A. Burris, D. Castellano, C. Canil, J. Bellmunt, D. Bajorin, D. Nickles, R. Bourgon, G. M. Frampton, N. Cui, S. Mariathasan, O. Abidoye, G. D. Fine, R. Dreicer, Atezolizumab in patients with locally advanced and metastatic urothelial carcinoma who have progressed following treatment with platinum-based chemotherapy: a single-arm, multicentre, phase 2 trial. *Lancet* 387, 1909-1920 (2016).

J. Liu, D. Chen, G. D. Nie, Z. Dai, CD8+CD122+ T-cells: a newly emerging regulator with central memory cell phenotypes. *Front Immunol.* 6, 494 (2015).

J. Naidoo, D. B. Page, B. T. Li, L. C. Connell, K. Schindler, M. E. Lacouture, M. A. Postow, J. D. Wolchok, Toxicities of the anti-PD-1 and anti-PD-L1 immune checkpoint antibodies. *Ann. Oncol., mdv*383 (2015).

J. Park, S. H. Wrzesinski, E. Stern, M. Look, J. Criscione, R. Ragheb, S. M. Jay, S. L. Demento, A. Agawu, P. L. Limon, Combination delivery of TGF-β inhibitor and IL-2 by nanoscale liposomal polymeric gels enhances tumour immunotherapy. *Nat. Mater.* 11, 895-905 (2012).

J. Vakkila, M. T. Lotze, Inflammation and necrosis promote tumour growth. *Nat. Rev. Immunol.* 4, 641-648 (2004).

K. Abiko, N. Matsumura, J. Hamanishi, N. Horikawa, R. Murakami, K. Yamaguchi, Y Yoshioka, T. Baba, I. Konishi, M. Mandai, IFN-γ from lymphocytes induces PD-L1 expression and promotes progression of ovarian cancer. *Br. J. Cancer* 112, 1501-1509 (2015).

K. D. Moynihan, C. F. Opel, G. L. Szeto, A. Tzeng, E. F. Zhu, J. M. Engreitz, R. T. Williams, K. Rakhra, M. H. Zhang, A. M. Rothschilds, S. Kumari, R. L. Kelly, B. H. Kwan, W. Abraham, K. Hu, N. K. Mehta, M. J. Kauke, H. Suh, J. R. Cochran, D. A. Lauffenburger, K. D. Wittrup, D. J. Irvine, Eradication of large established tumors in mice by combination immunotherapy that engages innate and adaptive immune responses. *Nat. Med.* 22, 1402-1410 (2016).

K. Kagawa, S. Tomizawa, Exocytotic excretion of dextran sulfates from liver to bile. *Jpn. Pharmacol.* 30, 101-108 (1980).

L. E. Klevorn, R. M. Teague, Adapting Cancer Immunotherapy Models for the Real World. *Trends Immunol.* 37, 354-363 (2016).

L. Galluzzi, A. Buque, O. Kepp, L. Zitvogel, G. Kroemer, Immunogenic cell death in cancer and infectious disease. *Nat. Rev. Immunol.* 17, 97-111 (2017).

L. Gu, D. J. Mooney, Biomaterials and emerging anticancer therapeutics: engineering the microenvironment. *Nat. Rev. Cancer* 16, 56-66 (2016).

L. Z. Shi, T. Fu, B. Guan, J. Chen, J. M. Blando, J. P. Allison, L. Xiong, S. K. Subudhi, J. Gao, P. Sharma, Interdependent IL-7 and IFN-[gamma] signalling in T-cell controls tumour eradication by combined [alpha]-CTLA-4+[alpha]-PD-1 therapy. *Nat. Comm.* 7, (2016).

M. A. Kursunel, G. Esendagli, The untold story of IFN-gamma in cancer biology. *Cytokine Growth Factor Rev.* 31, 73-81 (2016).

M. Black, I. B. Barsoum, P. Truesdell, T. Cotechini, S. K. Macdonald-Goodfellow, M. Petroff, D. R. Siemens, M. Koti, A. W. Craig, C. H. Graham, Activation of the PD-1/PD-L1 immune checkpoint confers tumor cell chemoresistance associated with increased metastasis. *Oncotarget* 7, 10557-10567 (2016).

M. E. van Rossen, W. Sluiter, F. Bonthuis, H. Jeekel, R. L. Marquet, C. H. van Eijck, Scavenging of reactive oxygen species leads to diminished peritoneal tumor recurrence. *Cancer Res.* 60, 5625-5629 (2000).

M. Mandai, J. Hamanishi, K. Abiko, N. Matsumura, T. Baba, I. Konishi, Dual Faces of IFNgamma in Cancer Progression: A Role of PD-L1 Induction in the Determination of Pro- and Antitumor Immunity. *Clin. Cancer Res.* 22, 2329-2334 (2016).

N. A. Hotaling, L. Tang, D. J. Irvine, J. E. Babensee, Biomaterial Strategies for Immunomodulation. *Annu. Rev. Biomed. Eng.* 17, 317-349 (2015).

N. Antonio, M. L. Bonnelykke-Behmdtz, L. C. Ward, J. Collin, I. J. Christensen, T. Steiniche, H. Schmidt, Y. Feng, P. Martin, The wound inflammatory response exacerbates growth of pre-neoplastic cells and progression to cancer. *EMBO J.* 34, 2219-2236 (2015).

N. McGranahan, A. J. Furness, R. Rosenthal, S. Ramskov, R. Lyngaa, S. K. Saini, M. Jamal-Hanj ani, G. A. Wilson, N. J. Birkbak, C. T. Hiley, T. B. Watkins, S. Shafi, N. Murugaesu, R. Mitter, A. U. Akarca, J. Linares, T. Marafioti, J. Y Henry, E. M. Van Allen, D. Miao, B. Schilling, D. Schadendorf, L. A. Garraway, V. Makarov, N. A. Rizvi, A. Snyder, M. D. Hellmann, T. Merghoub, J. D. Wolchok, S. A. Shukla, C. J. Wu, K. S. Peggs, T. A. Chan, S. R. Hadrup, S. A. Quezada, C. Swanton, Clonal neoantigens elicit T cell immunoreactivity and sensitivity to immune checkpoint blockade. *Science* 351, 1463-1469 (2016).

N. Reznikov, J. A. M. Steele, P. Fratzl, M. M. Stevens, A materials science vision of extracellular matrix mineralization. *Nat. Rev. Mater.* 1, 16041 (2016).

N. S. Katheder, R. Khezri, F. O'Farrell, S. W. Schultz, A. Jain, M. M. Rahman, K. O. Schink, T. A. Theodossiou, T. Johansen, G. Juhasz, D. Bilder, A. Brech, H. Stenmark, T.

E. Rusten, Microenvironmental autophagy promotes tumour growth. *Nature* 541, 417-420 (2017).

P. Sharma, J. P. Allison, Immune checkpoint targeting in cancer therapy: toward combination strategies with curative potential. *Cell* 161, 205-214 (2015).

P. Sharma, J. P. Allison, The future of immune checkpoint therapy. *Science* 348, 56-61 (2015).

P. Zhang, D. M. Su, M. Liang, J. Fu, Chemopreventive agents induce programmed death-1-ligand 1 (PD-L1) surface expression in breast cancer cells and promote PD-L1-mediated T cell apoptosis. *Mol. Immunol.* 45, 1470-1476 (2008).

R. A. Seder, P. A. Darrah, M. Roederer, T-cell quality in memory and protection: implications for vaccine design. *Nat. Rev. Immunol.* 8, 247-258 (2008).

R. Demicheli, M. Retsky, W. Hrushesky, M. Baum, I. Gukas, The effects of surgery on tumor growth: a century of investigations. *Ann. Oncol., mdn*386 (2008).

S. B. Stephan, A. M. Taber, I. Jileaeva, E. P. Pegues, C. L. Sentman, M. T. Stephan, Biopolymer implants enhance the efficacy of adoptive T-cell therapy. *Nat. Biotechnol.* 33, 97-101 (2015).

S. Bohm, A. Montfort, O. M. Pearce, J. Topping, P. Chakravarty, G. L. Everitt, A. Clear, J. R. McDermott, D. Ennis, T. Dowe, A. Fitzpatrick, E. C. Brockbank, A. C. Lawrence, A. Jeyarajah, A. Z. Faruqi, I. A. McNeish, N. Singh, M. Lockley, F. R. Balkwill, Neoadjuvant Chemotherapy Modulates the Immune Microenvironment in Metastases of Tubo-Ovarian High-Grade Serous Carcinoma. *Clin. Cancer Res.* 22, 3025-3036 (2016).

S. Kitano, K. Kataoka, Y. Koyama, T. Okano, Y. Sakurai, Glucose-responsive complex formation between poly (vinyl alcohol) and poly (N-vinyl-2-pyrrolidone) with pendent phenylboronic acid moieties. *Makromol. Chem. Rapid Comm.* 12, 227-233 (1991).

S. L. Topalian, J. M. Taube, R. A. Anders, D. M. Pardoll, Mechanism-driven biomarkers to guide immune checkpoint blockade in cancer therapy. *Nat. Rev. Cancer* 16, 275-287 (2016).

S. P. Arlauckas, C. S. Garris, R. H. Kohler, M. Kitaoka, M. F. Cuccarese, K. S. Yang, M. A. Miller, J. C. Carlson, G. J. Freeman, R. M. Anthony, In vivo imaging reveals a tumor-associated macrophage—mediated resistance pathway in anti-PD-1 therapy. *Sci. Transl. Med.* 9, eaal3604 (2017).

T. Doi, T. Okayama, T. Ishikawa, K. Oka, N. Sakamoto, T. Yasuda, Y. Naito, Y. Itoh. (AACR, 2015).

T. Konno, K. Ishihara, Temporal and spatially controllable cell encapsulation using a water-soluble phospholipid polymer with phenylboronic acid moiety. *Biomaterials* 28, 1770-1777 (2007).

T. N. Schumacher, R. D. Schreiber, Neoantigens in cancer immunotherapy. *Science* 348, 69-74 (2015).

T. Walzer, C. Arpin, L. Beloeil, J. Marvel, Differential in vivo persistence of two subsets of memory phenotype CD8 T cells defined by CD44 and CD122 expression levels. *J. Immunol.* 168, 2704-2711 (2002).

T. YAMAOKA, Y. TABATA, Y. IKADA, Comparison of Body Distribution of Poly (vinyl alcohol) with Other Water-soluble Polymers after Intravenous Administration. *J. Pharm. Pharmacol.* 47, 479-486 (1995).

V. A. Boussiotis, Molecular and Biochemical Aspects of the PD-1 Checkpoint Pathway. *N. Engl. J. Med.* 375, 1767-1778 (2016).

W. Ceelen, P. Pattyn, M. Mareel, Surgery, wound healing, and metastasis: Recent insights and clinical implications. *Crit. Rev. Oncol. Hematol.* 89, 16-26 (2014).

W. Zou, J. D. Wolchok, L. Chen, PD-L1 (B7-H1) and PD-1 pathway blockade for cancer therapy: Mechanisms, response biomarkers, and combinations. *Sci. Transl. Med.* 8, 328rv324 (2016).

Y. Kaneo, S. Hashihama, A. Kakinoki, T. Tanaka, T. Nakano, Y. Ikeda, Pharmacokinetics and biodisposition of poly (vinyl alcohol) in rats and mice. *Drug Metab. Pharmacokinet.* 20, 435-442 (2005).

Y Zhang, S. Choksi, K. Chen, Y Pobezinskaya, I. Linnoila, Z. G. Liu, ROS play a critical role in the differentiation of alternatively activated macrophages and the occurrence of tumor-associated macrophages. *Cell Res.* 23, 898-914 (2013).

What is claimed is:

1. A method of treating a non-immunogenic cancer in a subject comprising administering to the subject a hydrogel matrix comprising gemcitabine and an anti-PD-1/PD-L1 antibody; wherein the hydrogel matrix comprises a reactive oxygen species (ROS) degradable hydrogel that releases the gemcitabine and the anti-PD-1/PD-L1 antibody into the tumor microenvironment upon exposure to factors within the microenvironment.

2. The method of claim 1, wherein the anti-PD-1/PD-L1 antibody is selected from the group consisting of nivolumab, pembrolizumab, pidilizumab, atezolizumab, avelumab, durvalumab, and BMS-936559.

3. The method of claim 1, wherein the hydrogel releases the gemcitabine and the anti-PD-1/PD-L1 antibody into the tumor microenvironment for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

4. The method of claim 1, wherein the cancer is a cancer with low PD-L1 expression or a non-immunogenic cancer selected from the group consisting of melanoma, non-small cell lung carcinoma, renal cancer, head and neck cancer, and bladder cancer.

* * * * *